US008125640B2

(12) United States Patent
Abbott et al.

(10) Patent No.: US 8,125,640 B2
(45) Date of Patent: Feb. 28, 2012

(54) AUTOMATED ANALYSIS SYSTEM FOR DETECTION AND QUANTIFICATION OF BIOMOLECULES BY MEASUREMENT OF CHANGES IN LIQUID CRYSTAL ORIENTATION

(75) Inventors: Nicholas L. Abbott, Madison, WI (US); Aaron M. Lowe, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 519 days.

(21) Appl. No.: 12/380,751

(22) Filed: Mar. 3, 2009

(65) Prior Publication Data
US 2009/0262350 A1  Oct. 22, 2009

Related U.S. Application Data

(60) Provisional application No. 61/067,890, filed on Mar. 3, 2008.

(51) Int. Cl.
  *G01J 4/00* (2006.01)
  *G01N 31/00* (2006.01)
(52) U.S. Cl. ............. 356/364; 436/4; 436/164; 436/165
(58) Field of Classification Search ........................ None
See application file for complete search history.

(56) References Cited

U.S. PATENT DOCUMENTS 5,966,195 A * 10/1999 Sato et al. ..................... 356/367
(Continued)

OTHER PUBLICATIONS

Shah et al., Orientational Transitions of Liquid Crystals Driven by Binding of Organoamines to Carboxulic Acids Presented at Surfaces with Nanometer-Scale Topography, 2003, American Chemical Society, vol. 19 No. 2, pp. 275-284.*
Bernard et al., Nat. Biotechnol. (2001) 19, 866-869.
Canaria et al., Lab Chip (2006) 6, 289-295.
Clare et al., Langmuir (2006) 22, 4654-4659.

(Continued)

*Primary Examiner* — Gregory J Toatley
*Assistant Examiner* — Juan D Valentin
(74) *Attorney, Agent, or Firm* — Quarles & Brady LLP

(57) ABSTRACT

The present invention provides systems and methods for data acquisition and image analysis that utilize twisted nematic liquid crystals ("TNLCs") to create maps of bio/chemical functionality patterned on surfaces. The method involves the acquisition of a series of images of TNLC film that contacts the analytic surface followed by analysis of the series of images to yield maps of twist angle of the liquid crystal across the surface. This analysis technique effectively condenses a large data set (stack of images) into a compact form (map of twist angle), revealing features on the surface that were not apparent in the individual images comprising the original stack.

24 Claims, 19 Drawing Sheets
(13 of 19 Drawing Sheet(s) Filed in Color)

U.S. PATENT DOCUMENTS

| | | | | |
|---|---|---|---|---|
| 6,081,337 A * | 6/2000 | Kwok et al. | | 356/365 |
| 6,157,448 A * | 12/2000 | Kowa et al. | | 356/365 |
| 7,034,940 B1 * | 4/2006 | Hirosawa | | 356/369 |
| 7,583,853 B2 * | 9/2009 | Taylor et al. | | 382/276 |
| 7,629,174 B2 * | 12/2009 | Gu | | 436/164 |
| 7,745,220 B2 * | 6/2010 | Abbott et al. | | 436/165 |
| 7,808,637 B2 * | 10/2010 | Smith | | 356/367 |
| 2004/0185551 A1 * | 9/2004 | Niehaus | | 436/514 |
| 2006/0003389 A1 * | 1/2006 | Abbott et al. | | 435/7.9 |

OTHER PUBLICATIONS

Clare et al., Langmuir (2006) 22, 7776-7782.
Faetti et. al., Phys. Rev. Lett. (1985), 55; 16, 1681-1684.
Gupta et al., Science (1998) 279, 2077-2080.
Lien, Conference Record of the 1991 International Display Research Conference (1991) 192-194.
Lowe et al., Lab Chip (2008) 8, 1357-1364.
Tingey et al., Adv. Mater. (2004) 16, 1331-1336.

* cited by examiner

A)

B)

C)

A)

B)

C)

AUTOMATED ANALYSIS SYSTEM FOR DETECTION AND QUANTIFICATION OF BIOMOLECULES BY MEASUREMENT OF CHANGES IN LIQUID CRYSTAL ORIENTATION

CROSS-REFERENCE TO RELATED APPLICATIONS

This application claims benefit of U.S. Application No. 61/067,890, filed Mar. 3, 2008, which is incorporated by reference herein in its entirety.

STATEMENT REGARDING FEDERALLY SPONSORED RESEARCH

This invention was made with government support under CA108467 awarded by the National Institutes of Health. The government has certain rights in the invention.

FIELD OF THE INVENTION

The present invention is related to the field of liquid crystal-based detection systems. More particularly, the invention is directed to an automated system and method for determining the orientation of liquid crystals with high spatial resolution across a surface used in an analytic device.

BACKGROUND OF THE INVENTION

Recent studies have demonstrated that a range of molecular-level events at surfaces can be amplified into ordering transitions in thin films of nematic liquid crystals ("LCs"), thus enabling these molecular events to be reported as measurable changes in the optical appearance of the LCs. The approach uses the long range ordering of molecules within the liquid crystalline phase to amplify nanoscopic events at a surface into ordering transitions in the LC that occur on the optical (micrometer) scale. In the context of bioanalytic technologies, LC-based reporting of surface events offers potential means to routinely to validate surface chemical transformations that are central to the development and manufacture of surface array-based analytic devices. When combined with surfaces that presenting binding groups, this approach also has potential merit as a means for target molecule detection because it does not rely upon complex instrumentation, and in the case of biomolecule detection, liquid crystal detection obviates the need for labeling of the target molecules with radioactive or fluorescent probes. It has been previously demonstrated that the ordering of LCs is sensitive to the presence of specific chemical functional groups, peptides, and proteins on surfaces, and, with few exceptions, the interpretation of the optical output generated by the LCs has been largely qualitative in nature.

As can be appreciated, it is highly desirable to obtain analytical methods based on LCs that provide simple and versatile procedures permitting quantitative and multiplexed measurements of LC response to molecular events on surfaces.

SUMMARY OF THE INVENTION

The present invention provides systems and methods for the acquisition and analysis of optical images formed by thin films of liquid crystals (LCs) placed into contact with surfaces patterned with bio/chemical functionality relevant to surface-based assays. The methods are shown to determine chemical transformations on surfaces that are widely exploited in the preparation of analytic devices. Such chemical transformations can be shown by providing easily interpreted maps of such transformations.

Systems and methods according to the invention involve acquisition of multiple images of the LC as a function of the orientation of a polarizer and data analysis which condenses the information present in the stack of images to determine the distortion (such as twist angle) of the LC on the analytic surface. A preferred embodiment of the invention determines a twist distortion of the liquid crystal as a function of position across the surface. In one aspect of this embodiment, the distortion is shown in the form of a spatial map of the distortion of the liquid crystal. The invention facilitates image acquisition and liquid crystal analysis which can be fully automated in order to produce a complete analysis instrument. The present invention therefore provides a sensitive detector for a wide range of biomolecules including but not limited to DNA, protein, and peptides. As well, the invention facilitates non-destructive methods to monitor and validate chemical transformations on surfaces of the type that are routinely employed in the preparation of surface-based analytic technologies.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Figure 1:
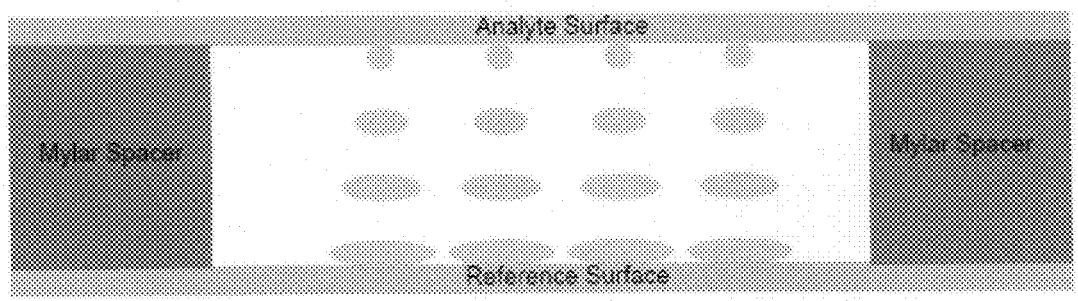
FIG. 1. Geometry of a twisted liquid crystal cell.

The present invention will now be described by reference to a preferred embodiment of the invention. Referring to FIG. 1, a system according to the invention consists of a liquid crystal cell and an automated image recording and analysis system. The liquid crystal molecules can be oriented by a variety of mechanisms, and in this embodiment, a liquid crystal cell is composed of two thin films of gold, chemically functionalized, facing each other, with a mylar spacer between them. By design, one surface orients the liquid crystal with an in-plane anchoring which is not parallel to the in-plane anchoring of the opposing surface. The automated analysis system precisely determines the in-plane liquid crystal orientation on both the reference surface and analyte surface, at all points simultaneously.

Figure 2:
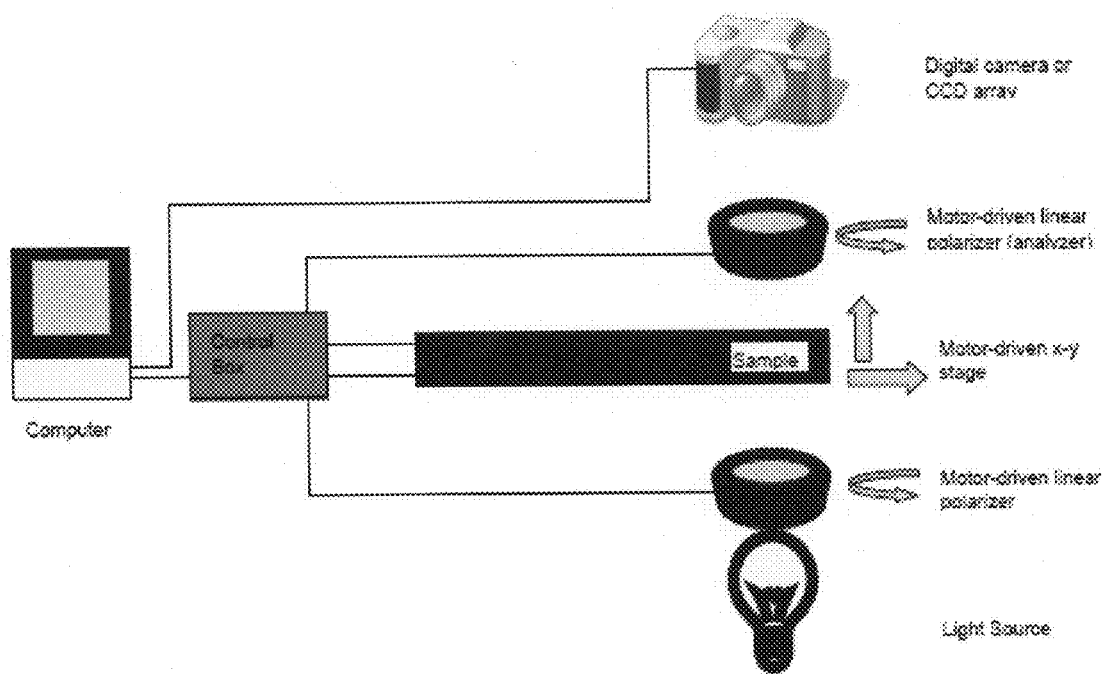
FIG. 2. Components of the automated analysis system.

FIG. 2 depicts the components of the preferred fully automated system. The orientation of the liquid crystal near the upper surface is calculated by an automated imaging system comprised of the following major components: a standard polarizing microscope equipped with a digital camera or CCD, computer, four positioning motors (for translational positioning of a liquid crystal sample and rotational positioning of a pair of linear polarizers), the liquid crystal cell, a control board to interface the positioning motors to the computer, and software to control the motors and camera and to analyze image data.

To determine the alignment of the liquid crystal near the reference surface, the analyzing polarizer is first rotated from the crossed-polar position. A suitable region is chosen for alignment purposes. This region will have little or no twist of liquid crystal orientation from reference to analyte surface. The two polarizers are then synchronously rotated in small steps and the resulting images analyzed to determine the rotational position that yields the lowest light intensity. This position of the polarizers sets the orientation of the reference surface to be parallel with respect to the polarizer. The analyzing polarizer is then automatically controlled and incrementally rotated, with an image of the liquid crystal cell taken at each increment. The images are subsequently processed using an algorithm which determines the orientation of the liquid crystal at the analyte surface with respect to the polarizer (and thus the reference surface) of the microscope for each picture element (pixel). The output is a matrix representing angles of orientation of the liquid crystal. In certain embodiments, this matrix can be visualized as a false color image. The sample can be translated by an x-y stage to yield a composite image of a surface area larger than the field of view.

Figure 3:
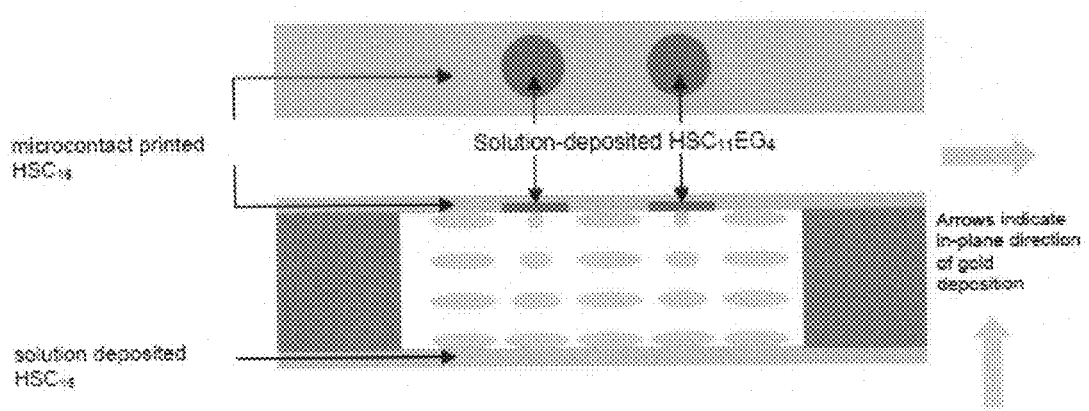
FIG. 3. Geometry of example liquid crystal cell for automated analysis.

In this embodiment, the procedure to measure the orientation of the liquid crystal is as follows. A gold substrate is produced by electron beam deposition of gold onto a cleaned glass surface at 60° to the surface normal of the glass. The gold is then functionalized with a chemical moiety of interest. One such functionality is achieved by immersion of the gold slide into a 1 mM solution of $HSC_{15}$ in ethanol, yielding a surface which orients the liquid crystal 5CB perpendicular to the in-plane direction of gold deposition. The opposing surface has gold deposited at 40° to the surface normal of the glass and is functionalized via microcontact printing of $HSC_{16}$ in a specific pattern such that a hydrophobic region is formed, which will confine an aqueous solution of $HSC11EG_4OH$ (EG4). The $HSC_{16}$ region will orient 5CB parallel to the in-plane direction of gold deposition, while the EG4 will orient 5CB perpendicular to the in-plane direction of gold deposition. As shown in FIG. 3, two such slides can be oriented such that the in-plane direction of gold deposition on each of them is perpendicular to one another. By holding the slides apart with a thin spacer (12 μm) and filling the cavity with 5CB heated above its clearing temperature and subsequently cooling the entire assembly to room temperature, a liquid crystal cell is produced that orients the liquid crystal planar to each surface. Furthermore, the in-plane orientation of the 5CB near the EG4 regions is perpendicular to the orientation of 5CB on the opposing $HSC_{15}$ surface, with a smooth, continuous transition between surfaces.

When such a liquid crystal cell is illuminated with a polarized light source, the polarization of the light will be rotated as it passes through the bottom of the cell and exits the top. The degree to which the polarization is rotated directly corresponds to the orientation of the liquid crystal and can be determined by rotating the analyzing polarizer until the light exiting the liquid crystal cell is extinguished. At this point of lowest intensity; the analyzer is oriented exactly perpendicular to the alignment direction of the liquid crystal at the analyte surface of the liquid crystal cell. To precisely determine the angle at which the light is extinguished, the intensity versus the angle of the analyzer can be fit to a function of the form $$f(x) = A\cos^2(x-\omega) \tag{A}$$

where f(x)=the intensity of the light, A=maximum intensity of light, x=analyzer angle, and ω=angle of minimum intensity.

To quantify intensity, color images are taken with a digital camera at several analyzer positions (from 0-180° at 10° intervals) and the images are converted from RGB color space to grayscale using the relation $$I = 0.299*R + 0.587*G + 0.114*B \tag{B}$$

where I=light intensity value of pixel, R=red intensity value of pixel, G=green intensity value of pixel, and B=blue intensity value of pixel.

Alternatively, the images can be acquired as grayscale intensity images without color information. After conversion to grayscale, Eq. (A) is fitted to each pixel value, over the range of analyzer positions from 0-180°, via a least squares minimization of Eq. (A) by varying the angle of minimum intensity. For a set of images taken at a spatial resolution of 640×480, this curve fitting is performed 640*480=307200 times. The spatial resolution and the number of angles imaged can be changed as necessary. The final output is, in essence, a false color image which allows for visual inspection of liquid crystal orientation at any one point, with high precision.

Figure 4:
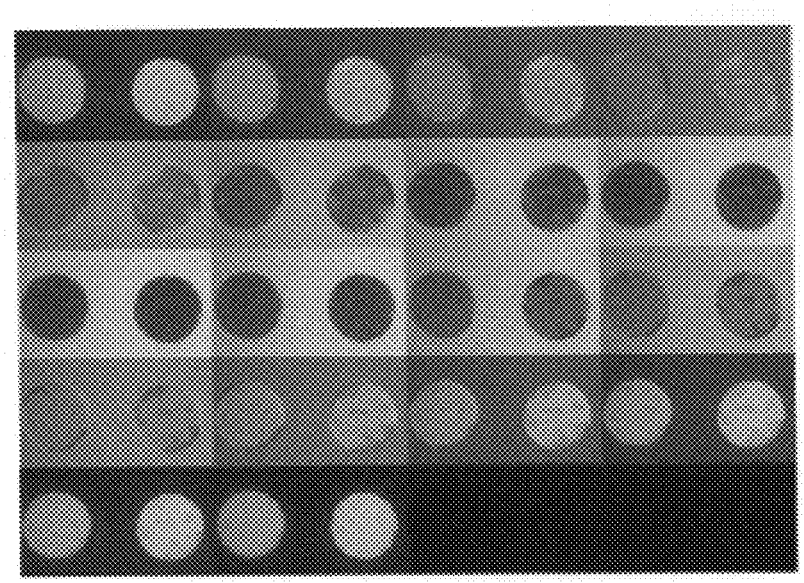
FIG. 4. Data for a liquid crystal cell configuration with perpendicular alignment of in-plane directions of gold deposition. A) Image sequence taken from 0°-180° analyzer orientation. The circles are 1 mm in diameter. B) Intensity plot with curve fitting for point 1,1 from 0°-180° C.) Output image of full analysis routine. The colors represent liquid crystal orientation derived from the analyzer position with the lowest intensity value ($\omega$).
Figure 4:
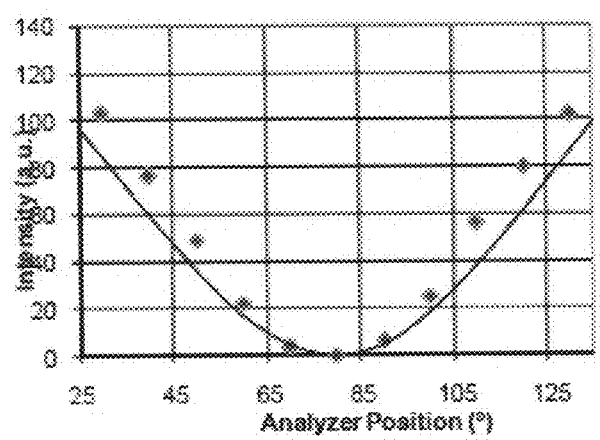
Figure 4:
Figure 4:
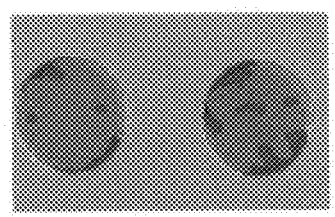

FIG. 4 shows a series of images taken for the aforementioned liquid crystal cell. A representative plot of light intensities is shown for pixel position 1,1 over a series of 18 analyzer angles from 0°-180°. The output matrix of the curve fitting routine is visualized with dark blue representing an orientation with respect to the polarizer of −90° and dark red representing an orientation with respect to the polarizer of 90°. Note that any angle with an absolute value larger than 90° is not meaningful, since −90° and 90° are indistinguishable orientations for a nematic liquid crystal.

Figure 5:
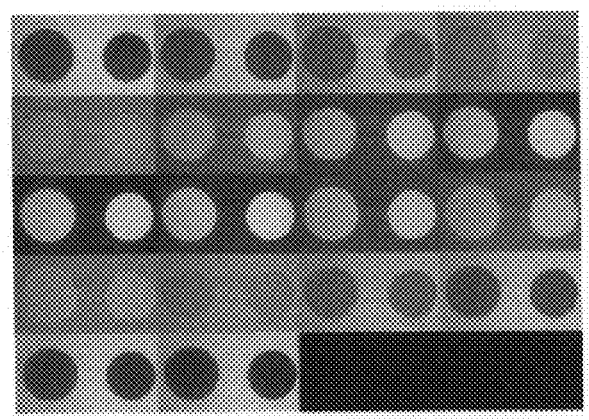
FIG. 5. Data for a cell configuration with parallel alignment of in-plane directions of gold deposition. A) Image sequence taken with analyzer oriented from 0°-180° analyzer orientation. B) Intensity plot with curve fitting for point 1,1 from 0°-180° analyzer orientation. C) Output image of full analysis routine. The colors represent liquid crystal orientation derived from the analyzer position with the lowest intensity value.
Figure 5:
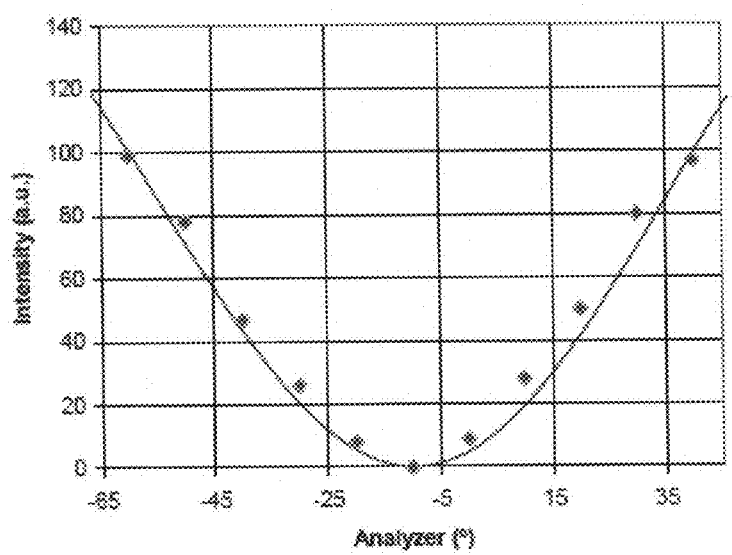
Figure 5:
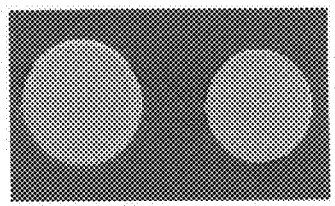

FIG. 5 depicts an analysis for a similar liquid crystal cell that was oriented such that the in-plane direction of gold deposition on each surface was nearly parallel. In the regions with EG4, the polarization shift from the bottom surface to the top should then be close to 0°.

Figure 6:
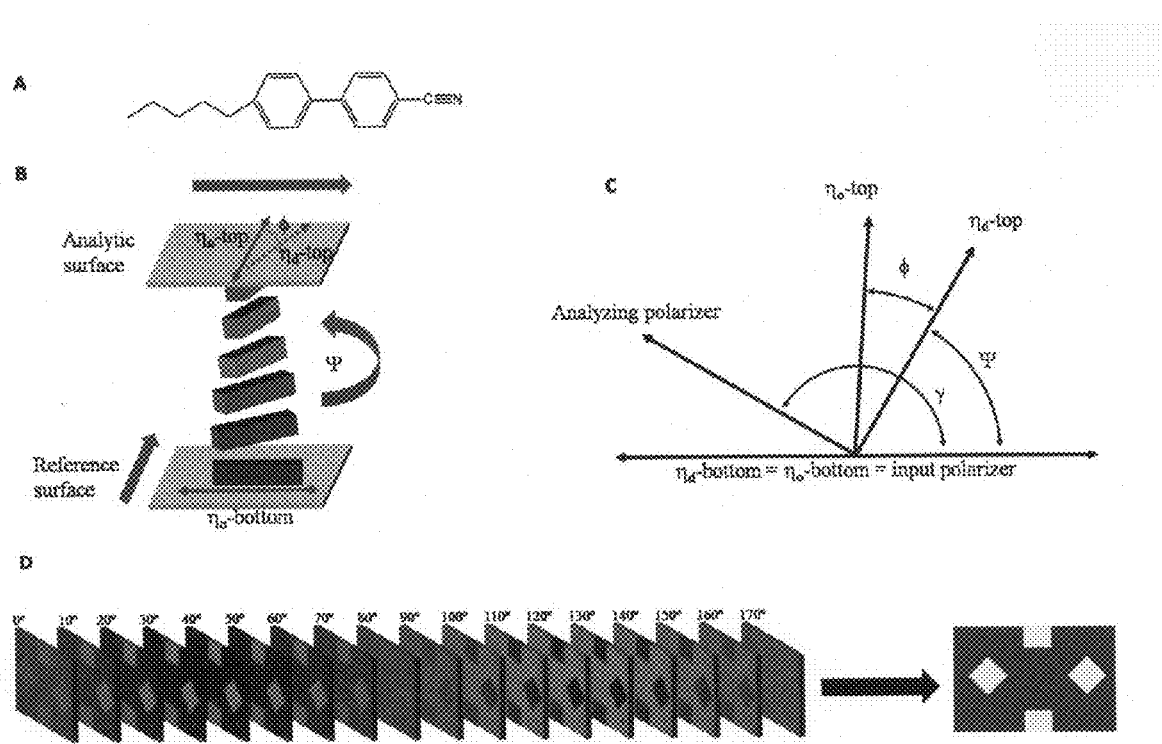
FIG. 6. (A) Molecular structure of 5CB (B) Schematic illustration of TNLC. Bold arrows indicate the in-plane direction of deposition of the gold films that confine the LC. The angles indicated in the diagram are defined in the text. (C) Diagram of the angles used to analyze the TNLC between two polarizers. (D) A stack of images of a TNLC obtained using orientations of the analyzer ranging from 0° to 170°. Image analysis condenses the information present in the stack of images into a single map of the twist angle over the entire surface.

As described above, and further illustrated in FIG. 6, a nematic LC such as 4'-pentyl-4-cyanobiphenyl ("5CB", FIG. 6A) may be confined between two surfaces that are structured so as to promote the LC to adopt mutually orthogonal orientations at the two confining surfaces (FIG. 6B). The interactions of the LC with the two confining surfaces cause a twist distortion to form within the LC. The angle of the twist distortion (Ψ in FIG. 6B) is determined by a competition between the elastic energy stored in the twisted state of the LC (which tends to minimize the twist angle) and the interaction energy of the LC with each surface (which promotes the orientation of the LC in preferred directions at the confining surfaces). Because of these competing effects, a decrease in the interaction energy of the LC with one of the confining surfaces will lead to an easily measured decrease in the twist angle of the LC.

It was previously demonstrated that LCs possessing a twist distortion (twisted nematic liquid crystals, "TNLC") can potentially provide an avenue to sensitive and quantitative analytic methods. It was also previously demonstrated that the interaction energy of LCs with surfaces (hereafter referred to as the anchoring energy of a LC) is very sensitive to the presence of molecular adsorbates, including molecules that are self-assembled into organized monolayers (SAMs) as well as biomolecules captured onto surfaces through specific interactions. In past studies, TNLCs were used to quantitatively report the presence of peptides and peptide-antibody interactions. Those studies, however, involved time-consuming procedures and were limited by the need for macroscopic surface areas with uniform chemistry. In contrast, the present invention is directed to general methods that are automatable and provide the added capability of imaging the spatial variation of the twist angle (and thus anchoring energy) of nematic LCs across patterned surfaces. The invention permits quantitative interpretation of the orientational response of LC molecules to changes in surface chemistry and biomolecular interactions on surfaces patterned with microarrays.

An additional embodiment of the invention is an analysis system for determining the distortion of a liquid crystal as a function of position across a surface, comprising: (a) a liquid crystal cell including a liquid crystal positioned between an analyte surface and a reference surface comprised of a surface to air, said surfaces spaced apart from each other such that the analyte surface orients the liquid crystal with an orientation that differs from the reference surface thereby introducing a distortion in the liquid crystal; and (b) an automated imaging system including: (i) an adjustable polarized light source to provide polarized light incident to the liquid crystal cell; (ii) an analyte linear polarizing device positioned to receive light passed through the liquid crystal cell, said analyte linear polarizing device adjustable with respect to polarization direction; (iii) an imaging device positioned to receive light passed through the analyte linear polarizing device from the liquid crystal cell; and (iv) one or more computer(s) interfaced with the analyte linear polarizing device, the computer(s) capable of receiving multiple image data from the imaging device and analyzing the multiple image data to determine the distortion of the liquid crystal contained within the liquid crystal cell as a function of position across one of the surfaces.

The above-described embodiment of the invention includes a thin film of liquid crystal supported on the analyte surface, where air or some other defined fluid is located in the region above the film of liquid crystal. In this embodiment of the invention the reference surface can be the free surface of the liquid crystal. It is well known to those skilled in the art that liquid crystals can assume defined orientations at free surfaces, and thus free surfaces can serve as reference surfaces in our invention provided the orientation of the liquid crystal is different at the free surface and analyte surface. For example, it is well known that the nematic liquid crystals 5CB and E7 assume a homeotropic orientation at their free surfaces. In one embodiment of this invention, the tilt angle of the liquid crystal at the analyte surface and the free surface will differ, thus satisfying the requirement of the invention that the orientation of the liquid crystal be different at the reference surface and analyte surface. It is well known by those skilled in the art that the tilt of the liquid crystal at the analytic surface can be determined by measuring the effective birefringence of a liquid crystal film of known thickness. An example is provided below.

Figure 7:
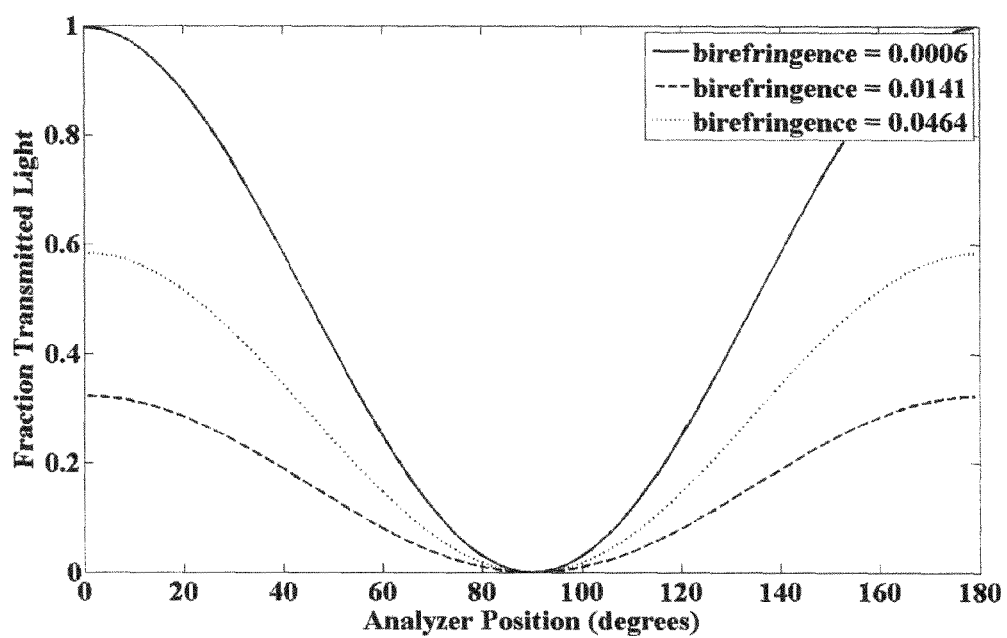
FIG. 7. Fraction of light transmission for a 10 μm thick layer of nematic liquid crystal as a function of analyzer position.

As a particular example of this embodiment, which should not be interpreted to be limiting the scope of this embodiment, a film of liquid crystal with a thickness of 10 µm is placed between two linear polarizing elements, and the intensity of transmitted light is then measured as a function of the angle of the analyzer. The liquid crystal is 5CB and is known to adopt a homeotropic orientation at the air-liquid crystal reference surface. FIG. 7 shows calculations of white light transmitted based upon Eq. (C) for three different birefringence values as the analyzer is rotated. The measurement of the intensity of transmitted light is used to calculate the effective birefringence and thus the orientation of the liquid crystal at the analyte surface at each location on the analyte surface. The orientation of the liquid crystal at each location on the analyte surface is used to calculate the anchoring energy on the analyte surface.

$$T = |AR(\Psi_2)R(-\phi)M(\phi,\Gamma/2)R(\Psi_1)E_{IN}| \quad \text{Eq. (C)}$$

In some embodiments, the light intensity is also measured for a reference region on the analyte sample, and the intensity of the transmitted light from each location on the analyte region is normalized by the reference region. In some embodiments of the invention, a suitable reference region is a region that causes the liquid crystal to assume an orientation parallel to the analyte surface (planar anchoring). For example, a self-assembled monolayer formed from pentadecanethiol on a gold film will cause planar anchoring of 5CB and thus can be a suitable reference region.

Figure 8:
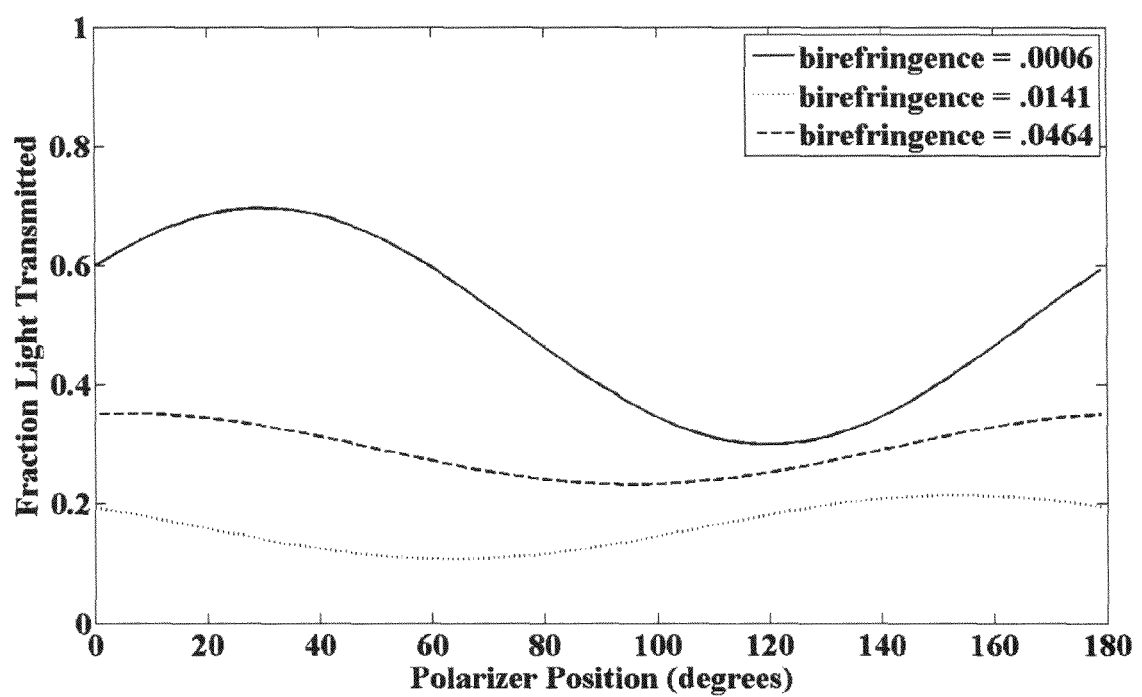
FIG. 8. Fraction of light transmission for a 10 μm thick layer of nematic liquid crystal as a function of incident polarizer position.

In yet another embodiment of the invention, the linear analyzer is replaced by a quarter-wave plate within the device described above. The easy axis of the sample is aligned with respect to the polarizer, and then the intensity of light transmitted through the system is measured as a function of incident polarizer. Analysis of the intensity of transmitted light according to the invention can be used to calculate the orientation of the liquid crystal at each location on the analyte surface. FIG. 8 shows calculations based upon this arrangement using Eq. (D) for white light.

$$T = |R(-\Psi_3)WR(\Psi_3)R(-\phi)M(\phi,\Gamma/2)R(\Psi_1)E_{IN}| \quad \text{Eq. (D)}$$

Eqs. (E)-(K) show the derivations of values used in Eq. (C) and Eq. (D). In Eqs. (C)-(K), T is the fraction of light transmitted, $E_{IN}$ is the Jones matrix for the incident polarizer, R is the Jones rotation matrix, M is the Jones matrix of the liquid crystal film, $\Delta n$ is the birefringence of the liquid crystal film, d is the thickness of the liquid crystal film, W is the Jones matrix for a quarter-wave plate, $\Psi_1$ is the orientation of the incident polarizer, $\Psi_2$ is the orientation of the analyzer, $\Psi_3$ is the orientation of the quarter-wave plate and $\phi$ is the twist of the liquid crystal.

$$E_{IN} = \begin{bmatrix} 1 \\ 0 \end{bmatrix} \quad \text{Eq. (E)}$$

$$R = \begin{bmatrix} \cos(.) & \sin(.) \\ -\sin(.) & \cos(.) \end{bmatrix} \quad \text{Eq. (F)}$$

$$M = \begin{bmatrix} \cos X - i\frac{\Gamma \sin X}{2X} & \phi \frac{\sin X}{X} \\ -\phi \frac{\sin X}{X} & \cos X + i\frac{\Gamma \sin X}{2X} \end{bmatrix} \quad \text{Eq. (G)}$$

$$X = \sqrt{\phi^2 + \left(\frac{\Gamma}{2}\right)^2} \quad \text{Eq. (H)}$$

$$\Gamma = \frac{2\pi\Delta n d}{\lambda} \quad \text{Eq. (I)}$$

$$W = \begin{bmatrix} e^{-i\frac{\pi}{4}} & \\ & e^{i\frac{\pi}{4}} \end{bmatrix} \quad \text{Eq. (J)}$$

$$A = \begin{bmatrix} \cos\Psi_2 \\ \sin\Psi_2 \end{bmatrix} \quad \text{Eq. (K)}$$

Although many techniques for the measurement of anchoring energies have been reported in the literature, the focus of these past studies has been directed to the development of surfaces for electro-optic LC displays and the methods are not easily applied to array-based surface analysis. The present invention is related to a methodology reported first by Clare et al. to measure the anchoring energy of nematic 5CB supported on chemically functionalized gold films. U.S. patent application Ser. No. 11/542,432, filed Oct. 3, 2006, which is incorporated herein by reference, describes devices and detection analyses related to Clare et al.'s respective methodology.

The method requires measurement of the intensity of light transmitted through a thin film of LC as a function of the orientation of the analyzer (FIGS. 6C and 6D). The measurement permits determination of the orientation of the LC at the analytic surface (top surface in FIG. 1B), $\eta_d$, and the angular deviation of the orientation of the LC (defined as $\phi$ FIG. 6B) from the so-called "easy axis", $\eta_o$, of the LC at the analytic surface. The easy axis of the analytic surface is defined as the orientation assumed by the LC in the absence of a torque generated by twist in the LC. Herein, the easy axis is defined by physical vapor deposition of thin gold films at an oblique angle of incidence, and by chemical functionalization of these gold films with ω-functionalized organothiols. For a LC film with a known twist elastic constant $K_{22}$ and thickness d, the anchoring energy may be calculated as $$W_{az} = \frac{2K_{22}\Psi}{d\sin(2\varphi)} \quad \text{Eq. (1)}$$

In the inventors' experiments, the anchoring energy of the LC on the reference surface is sufficiently high that the deviation of the LC from the easy axis of the reference surface is negligible.

In certain embodiment, anchoring energy can be optimized by changing various parameters of the liquid crystal cell to increase the sensitivity and precision of the invention. In preferred embodiments of the invention, the anchoring energy of the LC on the analyte surface ranges from about 0.01 μJm$^{-2}$ to about 10 μJm$^{-2}$. In more preferred embodiments, the anchoring energy ranges from about 0.01 μJm$^{-2}$ to about 5 μJm$^{-2}$. In preferred embodiments, the liquid crystal positioned between the analyte surface and the reference surface has a thickness from about 3 μm to about 50 μm. In more preferred embodiments, the liquid crystal positioned between the analyte surface and the reference surface has a thickness from about 6 μm to about 50 μm, with a most preferred thickness of about 15 μm. In certain embodiments, temperature control can be used to precisely regulate anchoring energy in order to increase the sensitivity and precision of the invention.

Whereas the methods reported by Clare et al. permitted the average angles $\Psi$ and $\phi$ in Eq. (1) to be determined using mm-sized areas of surfaces, the improvement provided by the present invention stems from the development of a generalized method of data acquisition and automated analysis such that accurate measurements of the twist angle can be obtained at each individual pixel of an image. There are several advantages to the methods reported here. First, because the output is a map of twist angle of the LC as a function of position, it is possible to characterize spatial variation in surface chemistry (including patterned surface chemistry such as that used to construct a microarray) with a resolution better than 10 μm. Second, the methods of data acquisition and image analysis are easily automated, thus allowing rapid and routine analysis of surfaces for imperfections or desired patterns of chemistry. The methodology preserves the advantages of highly parallel data acquisition that are inherent to methods based on optical imaging. Third, the creation of a map of twist angle as a function of position on a sample allows rapid identification of heterogeneities in a surface that are not apparent from an analysis of individual images of the LC obtained using a given setting of polarizer and analyzer. Fourth, as mentioned above, the interactions of LCs with surfaces are sensitive to variations in the chemistry of surfaces that are difficult to detect by other methods (e.g., ellipsometry and surface plasmon reflectometry). Accordingly, the methods described herein are useful for validation of chemically patterned surfaces used in surface-based analyses.

Additional embodiments of the present invention include the use of UV-visible absorption measurements to determine the thickness of the film of liquid crystal in a spatially resolved manner. The inventors have previously used UV-Vis spectroscopy to measure gaps between reflective surfaces (such as the liquid crystal cells used for twist analysis). This technique takes advantage of the interference that results when light is passed through the sample while continuously changing the wavelength. The behavior of this measurement is governed by the equation $$d = \frac{1}{2n}\left(\frac{1}{\frac{1}{2\lambda_2} - \frac{1}{2\lambda_1}}\right)$$

where d is the gap thickness, n is the index of refraction of the substance filling the gap, and $\lambda_2$ and $\lambda_1$ are the wavelengths of two consecutive minimum or maximum points of transmitted light intensity. Using a variable wavelength light source, it is possible to perform this type of analysis automatically, and in a spatially resolved manner, thus permitting the combination of this technique with the automated twist analysis for a spatially resolved measurement of liquid crystal anchoring energy.

A further embodiment of the invention involves preferred models for describing the passage of light through distorted liquid crystalline structures. The simplified equation (Eq. (2)) described herein is an approximate description of the passage of light and determination of the twist angle of the liquid crystal. Below a gap thickness of approximately 5.5 μm, this equation becomes inaccurate. A more accurate form of the equation is given by $$T = \cos^2(\psi - \gamma) - \sin^2\beta \begin{bmatrix} \sin^2 2\varphi \cos 2(\psi - \gamma) + \\ \frac{1}{2}\sin 4\varphi * \sin 2(\psi - \gamma) \end{bmatrix} +$$

$$\frac{\frac{1}{2}\psi \sin 2\beta \sin 2(\psi - \gamma)}{B} + \psi^2 \sin^2\beta[\sin^2(\psi - \gamma) - \sin^2\gamma]/\beta^2$$

where $\alpha = \pi \Delta n D/(\psi \lambda)$ and $\beta = \psi\sqrt{1+\alpha^2}$, $\Delta n$ is the liquid crystal birefringence, D is the liquid crystal thickness, and $\lambda$ is the light wavelength. This exact calculation is possible if the liquid crystal thickness is measured precisely.

It is further noted that the scope of the present invention includes automated sample alignment. Although manual sample alignment is useful and certainly encompassed by the present invention, in some situations such as high throughput production lines, it is preferred to automate the alignment. This process is routinely automated by using an algorithm that performs the procedure described in detail below in which the light transmission within a specific region of the optical cell is minimized by alternately rotating the analyzer and sample. The sample need not be rotated, as both the input polarizer and analyzer could both be rotated simultaneously to yield the same result.

Additional embodiments of the invention involve the automatic adjustment of the intensity of light incident on the liquid crystal. The input light intensity could automatically be adjusted to prevent image saturation. Although this is performed by hand in some embodiments of the invention, an automatic adjustment based on the intensity of light transmitted would make the entire analysis well-suited for a high throughput environment.

The following examples present results that validate methods of the invention for data acquisition and image analysis by using arrays of patterned self assembled monolayers ("SAMs") that orient LCs in known orientations. Second, examples are provided that show how the methodology can be used to report changes in surface properties resulting from transformations in the chemical functionality of surfaces. The potential utility of the method is illustrated by following (i) the displacement of a monolayer formed from one alkanethiol on a gold film by a second thiol in solution, and (ii) competitive adsorption processes involving mixtures of organothiols. Subsequent examples demonstrate how methods of the invention may be used to characterize biologically-relevant SAMs, including ethyleneglycol-terminated SAMs and amine-terminated SAMs. A further example describes an analysis of patterns of antibodies printed onto surfaces. An additional example demonstrates how various parameters of the liquid crystal cell of the invention can be varied to produce anchoring energies that optimize the sensitivity and precision of the measurements used in the invention. The final example shows the potential of using temperature control to produce more sensitive and/or precise results. The data disclosed in the examples, when combined, demonstrate that the LC-based image analysis method provided by the present invention offers a simple yet versatile means to characterize patterned surface chemical functionality relevant to bioanalytical technologies.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Materials and Methods

Materials. All materials were used as received, unless otherwise noted. Fisher's Finest glass slides were obtained from Fisher Scientific (Pittsburgh, Pa.). Gold (99.999% purity) was obtained from International Advanced Materials (Spring Valley, N.Y.). Titanium (99.99% purity) was obtained from PureTech (Brewster, N.Y.). Polished silicon wafers were purchased from Silicon Sense (Nashua, N.H.). Tetraethylene glycol-terminated thiol ($HS(CH_2)_{11}EG4$, referred to as EG4) and the corresponding amine-terminated thiol ($HS(CH_2)_{11}EG4NH_2$, referred to as EG4N) as a hydrochloride salt were obtained from Prochimia (Gdansk, Poland). Pentadecanethiol, hexadecanethiol, 2-aminoethanethiol hydrochloride (AET) and N-hydroxysuccinimide (NHS) were obtained from Sigma-Aldrich (Milwaukee, Wis.). 1-Ethyl-3-(3-dimethylaminopropyl)carbodiimide Hydrochloride (EDC) was obtained from Pierce Biotechnology (Rockford, Ill.). Liquid crystal 4'-pentyl-4-cyanobiphenyl (5CB) was obtained from EM Industries (New York, N.Y.), sold under the trademark name LICRISTAL (K15). Anhydrous ethanol containing 5% isopropyl alcohol and 5% methyl alcohol as denaturants was obtained from Sigma-Aldrich and purged with argon gas for 1 hour prior to use. Poly(dimethylsiloxane) (PDMS) elastomeric stamps were prepared using Sylgard 184 silicone elastomer kit obtained from Dow Corning (Midland, Mich.).

Protein solutions were prepared from phosphate buffered saline (PBS), pH 7.4 (Sigma-Aldrich, Cat #P3744). Biotinylated BSA was obtained from Pierce Biotechnology. Anti-biotin IgG and anti-rabbit IgG were obtained from Sigma-Aldrich.

Cleaning of Glass Substrates. Glass microscope slides were cleaned sequentially in piranha (70% $H_2SO_4$, 30% $H_2O_2$) and alkaline solution (70% KOH, 30% $H_2O_2$) for 1 h at ~80° C. The slides were then rinsed thoroughly with deionized water (18.2 $M\Omega$*cm), ethanol, and methanol and dried under a stream of nitrogen gas. The cleaned slides were stored in an oven at 110° C.

Preparation of Gold Substrates. Clean Glass Slides were Positioned within the chamber of an electron beam evaporator such that the incident angle of metal flux onto the substrate could be controlled. The incident angles ($\theta_i$, with respect to the surface normal) were measured with a digital level, with an accuracy of ±0.5°. All metal films were deposited at chamber pressures $<2\times10^{-6}$ torr at deposition rates of 0.2 Å/s. A thin film of titanium (thickness of 42-60 Å) was deposited onto the glass substrate to serve as an adhesion layer between the glass and semitransparent film of gold (thickness of 105-140 Å). All gold substrates were used within 1 h of removal from the evaporator chamber.

Formation of Patterned Self-Assembled Monolayers (SAMs). A PDMS elastomeric stamp with recessed features (squares and diamonds measuring 1 mm on each side, with depths of ~100 μm) was cast against a silicon master fabricated using standard photolithographic techniques. The master was silanized with (tridecafluoro-1,1,2,2,-tetrahydrooctyl)-1-trichlorosilane vapor (18 hours under vacuum) to aid in the release of the PDMS. After curing the PDMS for at least 18 h, the stamp was peeled from the master and ultrasonicated in a solution of 2:1 ethanol/water for 10 min×3 cycles. The surface of the PDMS stamps were inked with a 2 mM ethanolic solution of hexadecanethiol for 30 s and then dried with a stream of nitrogen gas. The PDMS stamp was placed into conformal contact with an obliquely deposited gold slide for 2 min. The slide surface was rinsed with ethanol, and then either (i) immersed into an ethanolic solution of an organothiol, or (ii) aqueous solutions of organothiols were applied to bare regions of the gold films (squares and diamonds). In the latter case, the hydrophobic SAM formed from hexadecanethiol served to confine the aqueous drops to the bare regions of the gold film. After incubation, slides were rinsed sequentially with copious amounts of ethanol, water, and ethanol, and then dried under a stream of gaseous nitrogen.

Fabrication of Affinity Stamps. Patterned PDMS stamps with raised features (300×300 μm squares, with heights of ~100 μm) were prepared in the manner described above. The PDMS stamps were oxidized using a PLASMATHERM 1441 RIE instrument (8 sccm $O_2$, 20 s, 100 W) to form a thin oxide layer on the stamp surface. The oxidized PDMS stamp was then functionalized with a primary amine by immersion into an aqueous solution of 10% 3-aminopropyltriethoxysilane at 80° C. for 1 h. The surface was rinsed copiously with water, dried with a stream of nitrogen and reacted with 0.1 M succinic anhydride in N,N-dimethylformamide at room temperature for 10 min to produce a carboxylic acid-terminated surface. Biotinylated BSA was immobilized onto the carboxylic acid groups using standard NHS/EDC chemistry.

Affinity Microcontact Printing. Patterned PDMS stamps presenting biotinylated BSA (prepared as described above) were incubated with 500 nM antibody in PBS for 2 h. The stamps were then rinsed sequentially with 0.05% v/v Triton X-100 in PBS for 10 s, PBS for 5 s, and water for 5 s followed by drying with a stream of nitrogen gas. The PDMS stamps were then contacted with gold films (deposited at an angle of 30° relative to the normal) that had been functionalized with 2-aminoethanethiol. The SAMs were rinsed with 0.01 M HCl and dried prior to contact printing. After 2 min of contact, the stamps were slowly removed from the gold films.

Fabrication of Optical Cells. Optical cells were fabricated by pairing an analytical surface with a reference surface such that the gold films were mutually oriented as depicted in FIG. 6B. The reference surface was a gold film (deposited at an angle of 64° relative to the surface normal) that was functionalized with pentadecanethiol. This type of surface strongly anchors the LC. The angle between the in-plane direction of gold deposition on the reference surface and analytic surface was 90° unless otherwise noted. The analytic surface and reference surface were spaced apart by 13 μm by using a thin film of Mylar. The cavity between the two surfaces was filled with 5CB heated into its isotropic phase (~50° C.). The optical properties of the LC cell were measured after cooling the cell to 25° C. for 30 min.

Measurement of the Twist Angle of the Liquid Crystal. The inventors measured the twist angle of the LC by adapting previously reported methods. Gupta, V. K. et al.; *Science* 1998, 279, 2077-2080; Clare, B. H. et al.; *Langmuir* 2006, 22, 4654-4659; Clare, B. H. et al.; *Langmuir* 2006, 22, 7776-7782, all of which are incorporated by reference herein. The optical cell containing the LC was placed between crossed polarizers with the input polarizer facing the reference surface. The easy axis of the LC on the reference surface was aligned to be parallel with the input polarizer using the technique described by Lien. Lien, A. *Conference Record of the 1991 International Display Research Conference* 1991, 192-194, which is incorporated by reference herein. Briefly, an iterative process was used to minimize the transmission of 546.5 nm light through the regions functionalized with hexadecanethiol on the analytic surface. This was accomplished by alternately rotating the sample between the stationary polarizers, followed by rotation of the analyzer. The transmission of light was minimized at each of the iterations. Three iterations were typically sufficient. Images were obtained using a polarized light microscope (BX60, Olympus) equipped with an X-Y translation stage and a digital camera (2.8 f-stop, 1/800 s shutter speed). Consistent settings of the light intensity were used (aperture set at one-half maximum, and lamp intensity set at two-tenths maximum) for individual samples. The lamp intensity was set at two-tenths of maximum to ensure that the images did not saturate during rotation of the analyzer. The analyzer was rotated at 10° increments, with images obtained at each analyzer position. The fraction of light transmitted through the optical cell, $T_{wg}$, was fit to the function $$T_{wg} = \cos^2(\Psi - \gamma) \quad \text{Eq. (2)}$$

where $\Psi$ is the twist angle of the LC (FIG. 1) and $\gamma$ is the position of the analyzer relative to the input polarizer ($\gamma$=0-170°). The fit was performed at each pixel of the family of images of each optical cell using an algorithm implemented in MATLAB (version 7.3.0, 2006b) to yield a 2-dimensional matrix with elements representing the values of the twist angle at each pixel. A color map of twist angle was calculated by correlating a specific color with each value of the twist angle.

Analysis Algorithm. All image analysis was performed with MATLAB version 7.3.0 R2006b. The images acquired at each position of the analyzer are read as matrices with dimensions i×j×k, where i is the horizontal number of pixels, j is the vertical number of pixels and k is the R, G, or B decomposition value of the image, on a scale of 0-255. The R,G,B values are converted into luminosity values using the equation $$I = 0.299*R + 0.587*G + 0.114*B$$

such that the luminosity is now represented by a i×j matrix with values on a scale of 0-255. The luminosity matrices are then used to create a matrix of the form i×j×k, with k now representing the analyzer position (18 positions in all, from 0-170°). For each value of i×j, the range of analyzer values (dimension k) was fit to Eq. (2) by first reducing all luminosity values such that the lowest value equals 0. The data are then fit to Eq. (2) using a linear least squares fitting routine. The fitting routine is constrained to result in twist angles between −90 and +90°. The result is a i×j matrix containing elements representing the twist angle at each pixel.

MATLAB is a proprietary software package designed to aid in engineering calculations. Although the inventors describe an embodiment of the invention which employs MATLAB (as specified below), alternative embodiments that utilize other software, aside from MATLAB, are possible. An alternative to MATLAB, called OCTAVE, was developed in the Department of Chemical and Biological Engineering at the University of Wisconsin in Madison. Additionally, the analysis algorithm used by the original implementation of the invention could be achieved using numerous programming languages (e.g. C++ or C#) or through dedicated hardware.

The steps needed to accomplish the most basic analysis used by the invention are as follows. (1) A series of images for each analyzer position (for example 0°-170° in 10° increments) are acquired through a digital camera controlled by a computer. (2) Using MATLAB, images are read into the computer memory in 3-D matrix form. (3) Using MATLAB, images are converted into gray scale intensity values. (4) Using MATLAB, the intensity values for each pixel position across the series of images (analyzer positions) are fitted to a function of the form $f(x)=A \cos^2(x-\omega)$, where A is a factor determined by the amplitude of the intensity values (see FIG. 4B), x is the analyzer position, and ω is the twist of the liquid crystal (the lowest value of the curve fitted in FIG. 4B). A is determined by taking the maximum intensity value of the data. ω is determined through a linear least squares fitting routine, in which the function $\text{Error}=\Sigma_{n=1}^{18}\{A\ [\cos(x_n-\omega)]^2-y_n\}^2$ is minimized by varying ω. This minimization is based on the Nelder-Mead simplex method for minimization of multiple variables (as implemented in MATLAB). Alternative minimization routines are available. In this example n=1 to 18, but this number can be changed, depending on the desired number of input images. At a minimum, n=3; at a maximum n=∞. (5) Using MATLAB, after the curve is fit and ω determined for one pixel position, the process is repeated for each pixel position, across the range of analyzer positions. (6) Using MATLAB, the output is stored as a matrix and a separate image is produced by assigning a different color value to each angle stored in the output matrix.

Example 2

Figure 9:
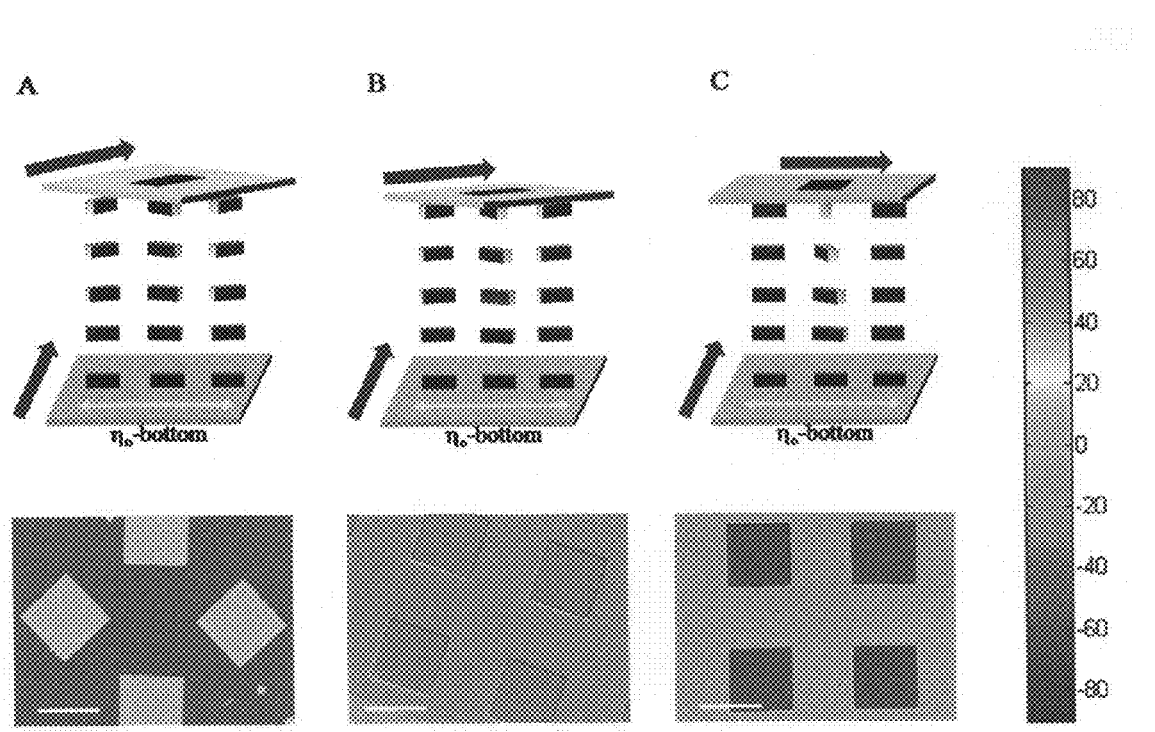
FIG. 9. Schematic representation of TNLCs (top) and corresponding maps of twist angles of the LC (bottom) obtained using analytic surfaces patterned with hexadecanethiol (continuous area of surface) and pentadecanethiol (squares). Twist angles of the LC corresponding to each color are indicated by the color chart shown at the right side of the figure. Bold arrows in the top diagrams indicate the in-plane direction of deposition of the gold films that confine the LC. The angle between the direction of deposition of the gold films in the analytic (top) and reference (bottom) surfaces of the cell was (A) 45°, (B) 60°, and (C) 90°. See text for details. Scale bars indicate 1 mm.

Validation of Data Acquisition and Image Analysis Using Surfaces that Generate Known Orientations of LCs The first experiments described below were performed in order to validate the data acquisition and image analysis methodology. For these experiments, the inventors used surfaces patterned with monolayers that gave rise to known orientations of the LC. The surfaces were prepared from semi-transparent gold films that were deposited by physical vapor deposition at an angle of incidence (measured from the surface normal) of either 64° (reference surface) or 49° (analytic surface). The surfaces were aligned with respect to each other so that the angle between the in-plane direction of deposition of gold on the reference surface and the analytic surface was nominally 45°, 60° or 90° (FIG. 9, top). These angles were estimated by eye-measurements reported below define the exact values. The reference surface was functionalized with a monolayer formed from pentadecanethiol; these monolayers cause the easy axis of the LC on the surface to be perpendicular to the in-plane direction of gold deposition (see bottom surfaces in FIG. 9). The analytic surfaces (top surfaces in FIG. 9) were patterned with hexadecanethiol by using microcontact printing. The hexadecanethiol causes the easy axis of the LC to be parallel to the in-plane direction of deposition of the gold. The stamp used for printing was designed to leave square regions on the gold film that were not functionalized with hexadecanethiol. These square regions (1 mm on a side) were subsequently functionalized with pentadecanethiol by immersion of the entire analytic surface into an ethanolic solution of pentadecanethiol for 10 mins. A film of LC was confined between the analytic and reference surfaces such that the thickness of the film of LC was nominally 13 μm.

Figure 10:
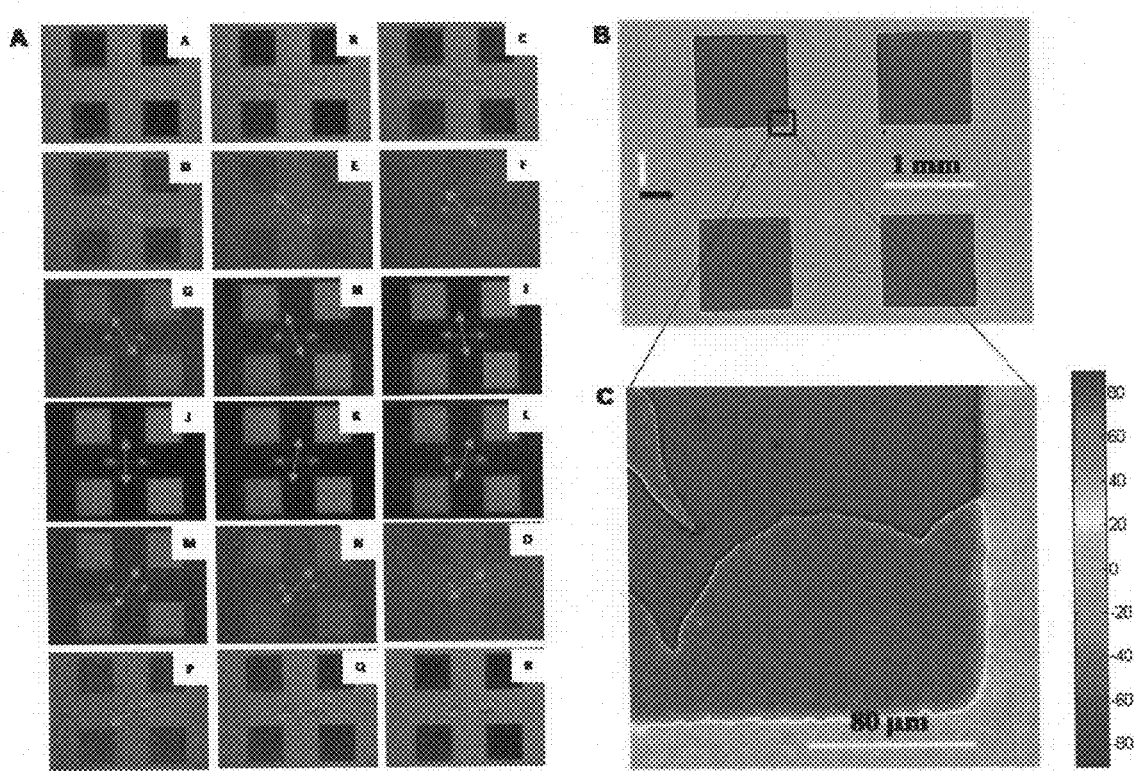
FIG. 10. (A) Images of TNLCs contacted with an analytic surface comprised of patterned pentadecanethiol (squares) and hexadecanethiol. Images A-R were obtained between two polarizers (transmission mode) as a function of the analyzer orientation (indicated by the green arrow). The input polarized orientation is indicated by the red arrow. (B) Map of twist angles obtained using a 4× objective lens. (C) Map of twist angle obtained using a 50× plan-view objective lens. Twist angles of the LC corresponding to each color are indicated by the color chart shown at the right side of the figure.

With the sample and input polarizer fixed in position as described in the Methods section, the analyzer was then rotated in 10° increments. An image was captured at each position of the analyzer, for a total of 18 images. FIG. 10A shows the set of 18 images obtained for the optical cell fabricated with a twist angle of approximately 45°. Inspection of FIG. 10A reveals that the intensity of transmitted light was modulated upon rotation of the analyzer by 90°, with nearly opposite phase for the regions of the analytic surface functionalized with hexadecanethiol (continuous area of surface) as compared to pentadecanethiol (squares). The change in intensity of transmitted light (as a function of angle of the analyzer) was used to calculate the twist angle of the LC at each pixel of these images, as described in the Methods section. This result is shown in FIG. 9A.

Inspection of FIG. 9A reveals that the LC in contact with the regions of the analytic surface functionalized with hexadecanethiol (blue areas) possessed an average twist of angle of $\Psi_{C16}=-52.4°\pm0.7°$. By assuming the anchoring of the LC on both the reference and analytic surface to be very strong (see below), the twist angle was used to calculate the angle between the in-plane direction of deposition of the gold films on the analytic surface and reference surface (δ) by using the relation $\delta=90°-|\Psi_{C16}|$. This calculation yields $\delta=37.6°\pm0.7°$ for this optical cell. The twist angle of the LC in contact with the surface formed from pentadecanethiol was calculated to be $\Psi_{C15}=36.2°\pm0.7°$. These results, when combined, indicate that the angle between the azimuthal orientation of the LC on the pentadecanethiol and hexadecanethiol surfaces is 88.6°±1.0°. The inventors note that if the analytic and reference surfaces both possessed infinite anchoring energies, the angle between the orientation of the LC on the pentadecanethiol and hexadecanethiol regions should be 90°. The above result (88.6°±1.0°) indicates that the SAMs do indeed possess very high anchoring energies.

The inventors also analyzed the optical cells prepared with nominal twist angles of 60° and 90°. The maps of twist angles of the LC for these samples are shown in FIGS. 9B and 9C, respectively. The twist angle of the LC in the pentanethiol-functionalized squares was measured to be 61.0°±0.7° for the nominally 60° twisted optical cell and 81.2°±0.8° for the nominally 90° twisted optical cell. The inventors measured the difference between twist angles in the pentanethiol- and hexadecanthiol-functionalized regions to be similar to that measured in the 45° twisted optical cell: −88.°±1.2° for the nominally 60° twisted optical and 87.8°±1.1° for the nominally 90° twisted optical cell. These results confirm strong anchoring of the LC on the surfaces used in these experiments.

The results above demonstrate accurate quantification of the twist angle of the LC at each pixel of the images obtained using the LCs, with each pixel representing an area of ~6 μm×6 μm over a field-of-view of 4 mm×3 mm (image size of 640×480 pixels). As shown in FIGS. 10B and 10C, higher resolution maps are attainable when an objective lens of higher magnification is used for image acquisition (50× objective and 1600×1200 pixels). These high resolution maps of twist angles reveal defect lines (disclinations) in the LC. These defects lie between regions of the LC that differ in the handedness of the twist distortion.

Example 3

Imaging of Displacement Reactions Involving Alkanethiols

Heterogeneity and poor reproducibility of surface chemistry are key issues that currently limit the development of quantitative surface-based microarray technologies. Few techniques are sufficiently simple to provide a means to routinely validate that surface chemistries have been deposited in patterns of the type typically used in multiplexed analytic technologies. As a model surface chemical transformation, the inventors sought to determine if it would be possible to follow the displacement of a self-assembled monolayer formed from an alkanethiol on a surface by a second alkanethiol in solution by using methods based on TNLCs.

This class of displacement reactions can limit the quality of chemical patterns that can be prepared by using SAMs formed from alkanethiols. In particular, the inventors investigated the displacement of a microcontact printed SAM formed from hexadecanethiol by an ethanolic solution of pentadecanethiol. These two SAMs differ only by one methylene group, and thus serve to demonstrate the subtle variations in surface chemistry that can be reported by using LCs.

Figure 11:
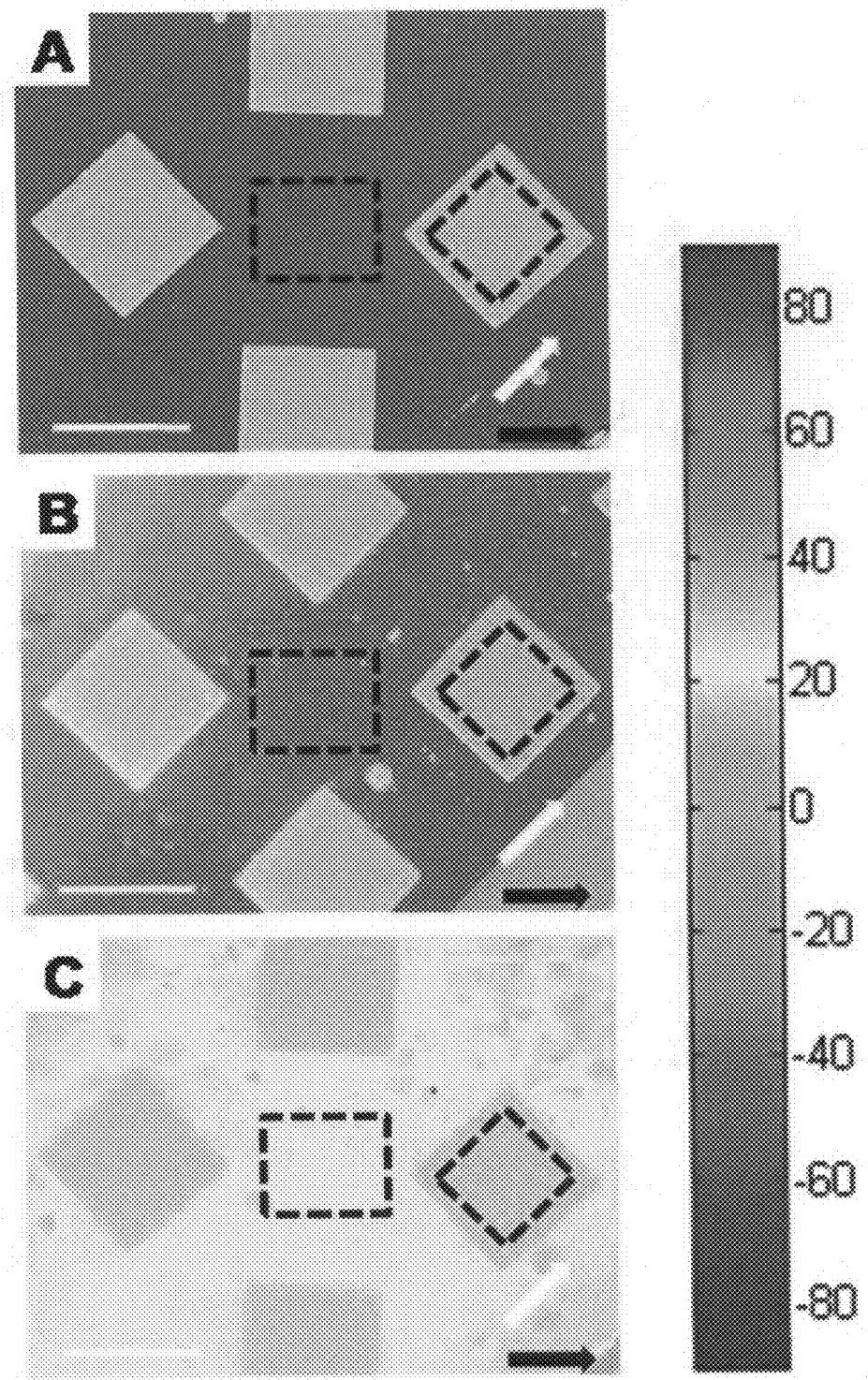
FIG. 11. Maps of twist angles of TNLCs in contact with analytic surfaces prepared by microcontact printing of hexadecanethiol, and subsequent immersion of the surfaces in pentadecanethiol solutions for (A) 10 mins, (B) 2 hrs, and (C) 24 hr. The squares correspond to regions of the gold films on which hexadecanethiol was not microcontact printed. The direction of deposition of the gold on the analytic and reference surfaces is indicated by the white arrows and black arrows, respectively. Twist angles of the LC corresponding to each color are indicated by the color chart shown at the right side of the figure. Scale bars represent 1 mm.

Using optical cells assembled in the same manner as those described in the previous section, the inventors compared the twist angles of LCs in contact with analytic surfaces prepared by microcontact printing of hexadecanethiol and subsequent immersion into ethanolic solutions of pentadecanethiol for periods of 10 minutes, 2 hours, or 24 hours. They predicted rapid formation of the SAM formed from pentadecanethiol on the bare gold regions of the microcontact printed surface (as was seen in the experiments described in FIGS. 9 and 10). In contrast, the inventors anticipated a slow process of displacement of the microcontact printed hexadecanethiol by the pentadecanethiol in solution. As shown in FIG. 11A, after immersion of the microcontact printed surface into an ethanolic solution of pentadecanethiol for a period of 10 minutes, the inventors observed orthogonal alignment of LC in the regions functionalized with pentadecanethiol (gold colored squares/diamonds) and in the regions microcontact printed with hexadecanethiol (blue background). A few small imperfections are evident in the area that was microcontact printed with hexadecanethiol These small circles are areas of the analytic surface that were not functionalized with hexadecanethiol due to particulate matter (dust) that prevented conformal contact of the PDMS stamp with the gold film. When the gold films patterned with hexadecanethiol were immersed in ethanolic solutions of pentadecanethiol for periods longer than 10 minutes, the inventors observed a reduction in the twist of the LC on the areas of the surface where the hexadecanethiol had been stamped (FIG. 11B). Inspection of FIG. 11B also shows that regions of the surface that were microcontact printed with hexadecanethiol are no longer homogeneous. They calculated the average twist angle of the LC at the center of each sample that had been microcontact printed with hexadecanethiol, and thereby determined that the twist angle changed from 88.6° to 74.4° to 8.7° (measured relative to the region formed from pentadecanethiol) following immersion in the solution of pentadecanethiol for 10 mins, 2 hrs and 24 hrs, respectively. In summary, these measurements of twist angles of the LC are consistent with the expected rapid formation of the SAM from pentadecanethiol on the bare gold regions of the microcontact printed surface, and a slow process of displacement of the microcontact printed hexadecanethiol by the pentadecanethiol in solution. More broadly, these results demonstrate the use of TNLCs to report displacement reactions involving adsorbates on surfaces even in cases where the two competing species are similar in structure.

Example 4

Imaging of Competitive Co-Adsorption of Mixtures of Organothiols

Mixed monolayers of alkanethiols are used widely to tune surface properties of gold films for bioanalytical assays. Commonly employed components of mixed SAMs formed on gold are $EG_n$-terminated alkanethiols (which resist non-specific protein adsorption) and $EG_n$-$NH_2$-terminated alkanethiols (used for covalent attachment of biomolecules). Mixed monolayers of these and other organothiols are typically formed by competitive coadsorption from solution. The composition of the mixed monolayer is generally dictated by the kinetics of the reaction at the surface (at least, for short reaction times). The presence of adventitious adsorbates (as influenced, for example, by the age of the gold films) and other factors that are not well understood can impact the kinetics, and thus reproducible preparation of mixed monolayers requires careful control of experimental conditions. Precise control over surface composition of mixed monolayers is important for the development of quantitative analytic technologies.

To explore the utility of methods based on TNLCs for the imaging of mixed monolayers, the inventors microcontact printed hexadecanethiol onto gold films, as described above. The resulting bare gold regions (1 mm×1 mm squares) were subsequently functionalized with monolayers of EG4 coadsorbed with either 2-aminoethanethiol*HCl (AET), or EG4N*HCl in various ratios (total organothiol concentration of 1 mM). The inventors investigated both AET and EG4N as the second component because (i) AET and EG4N both possess primary amine groups, but AET is a smaller molecule than EG4N; they predicted lower levels of incorporation of AET into mixed monolayers as compared to EG4N, and (ii) they have previously used monolayers of AET in LC-based assays for biomolecules. The inventors prepared mixtures of the thiols in a solvent comprised of water and ethanol (99:1). They used aqueous solutions (rather than the more commonly used anhydrous ethanol) in order to slow the rate of evaporation of the solutions (~250 mL) deposited as droplets in the 1 mm×1 mm squares on the surface. The analytical surface and reference surface were oriented such that the angle between the in-plane direction of gold deposition on the two surfaces was ~90°.

Figure 12:
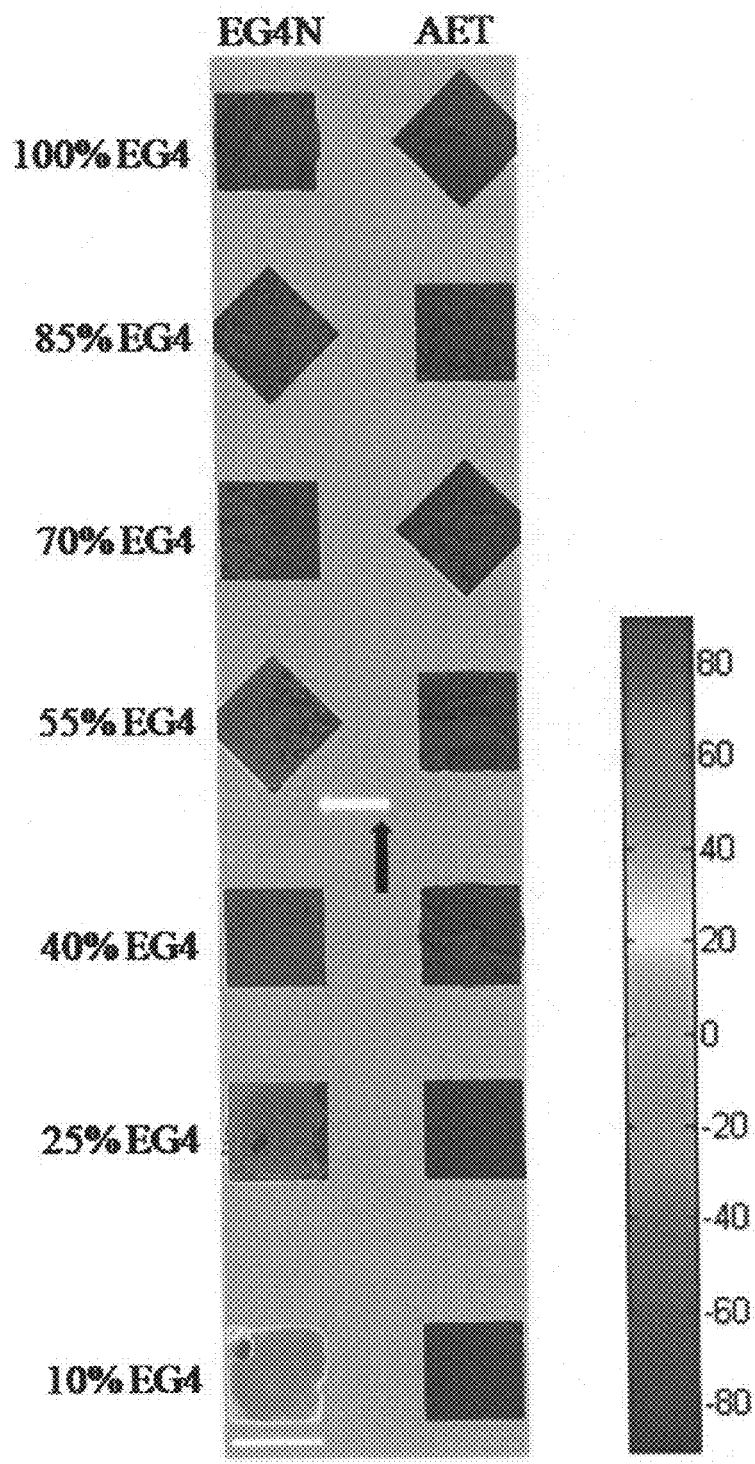
FIG. 12. Maps of twist angles of TNLCs on surfaces that were microcontact printed with hexadecanethiol and then functionalized with mixed monolayers (square regions) of either $EG_4$ and AET or $EG_4$ and EG4N. The composition of the mixed thiol solution used to form the monolayer is indicated to the left of the images. The direction of deposition of the gold on the analytic surface and reference surface is indicated by the white arrow and the black arrow, respectively. Twist angles of the LC corresponding to each color are indicated by the color chart shown at the right side of the figure. Scale bar (lower left) indicates 1 mm.

The spatial maps of the LC twist angles are shown in FIG. 12. The continuous green region (twist angle of 1.9°±0.6°) corresponds to the area of the surface where the hexadecanethiol was microcontact printed and indicates that the analytic and reference surfaces were oriented at 88.1°±0.6° with respect to each other. In most of the square-shaped regions of the surface, domains of opposite handed twist are evident as blue regions beside red regions. Single component monolayers of EG4 are known to orient nematic 5CB with an easy axis that is perpendicular to the in-plane direction of gold deposition, evident in FIG. 12 (top squares) as a twist angle of 87.9°±1.0°. The orientation of the 5CB on the EG4 monolayer deviates from the orientation of the easy axis by an angle of $\phi$=0.2°±1.2°, which indicates that the monolayer of EG4 causes strong anchoring of 5CB. A previous study concluded that SAMs of EG4 formed from aqueous solutions are more ordered than SAMs of EG4 deposited from ethanolic solutions. Canaria, C. A. et al.; *Lab Chip* 2006, 6, 289-295. The result shown in FIG. 12, when combined with the results of our past studies that used EG4 monolayers formed from ethanol (Clare, B. H. et al.; *Langmuir* 2006, 22, 4654-4659), suggests that the crystalline order of the monolayer may influence the anchoring energy of the LC.

Figure 13:
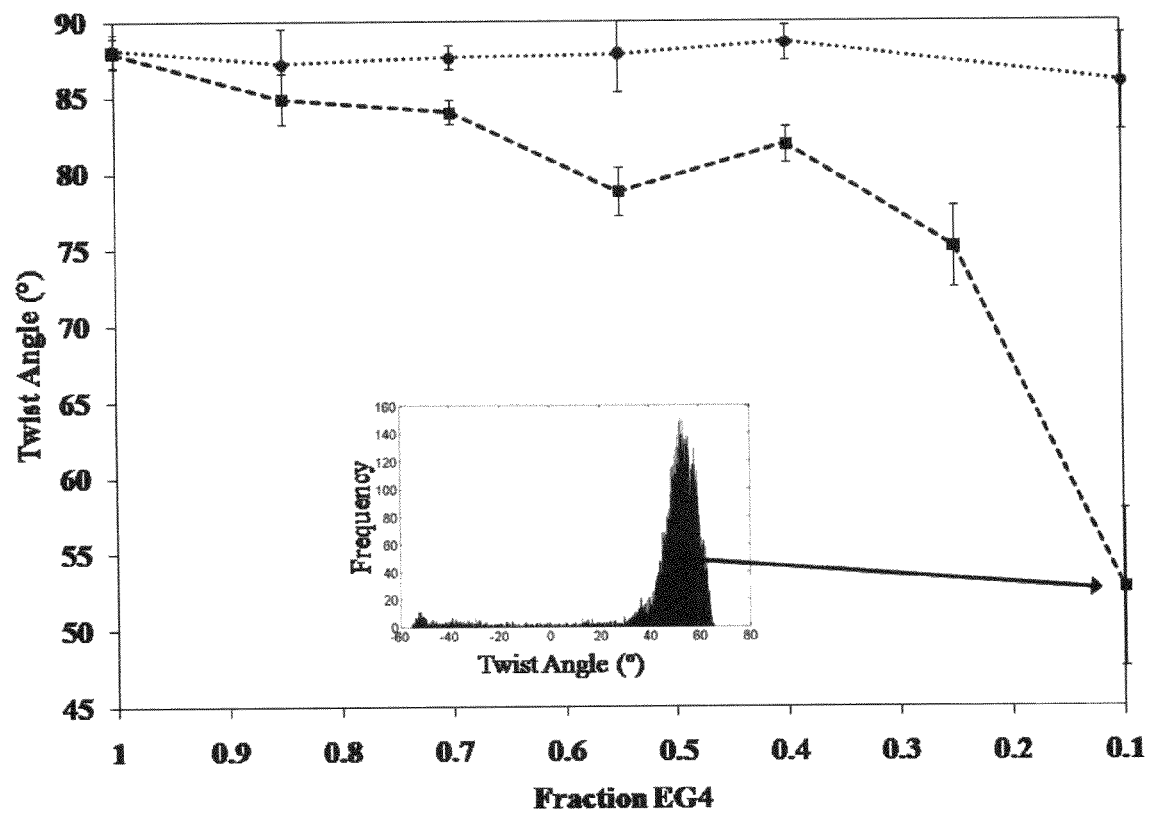
FIG. 13. Twist angles of the LC calculated from the images shown in FIG. 5. Data corresponding to the EG4/EG4N monolayers is represented by the filled squares; filled circles correspond to mixed monolayers of AET/EG4. The inset shows the distribution of twist angles within one of the analytic areas.

Inspection of FIG. 12 reveals that incorporation of EG4N into EG4 monolayers leads to a decrease in the twist angle. The inventors plot the twist angles of the red domains in FIG. 13. Only domains with a positive twist angle were plotted for the sake of clarity, but the trend was identical regardless of the handedness of the twist. They measured a twist angle of 52.8°±5.2° for the mixed monolayer formed from the solution containing 90% EG4N and 10% EG4-corresponding to a deviation of $\phi$=35.3°±5.2° from the easy axis. The large uncertainty in this measurement indicates a broad range of twist angles within the analytical area. This result highlights a useful attribute of the methodology reported herein, namely the ease with which heterogeneities can be detected over a large surface area. The inventors quantified the distribution of twist angles by plotting a histogram of the twist angles within an analytic area. The inset of FIG. 13 shows the histogram for the area functionalized with 90% EG4N. The inventors' measurements of the mixed monolayers of AET and EG4 were strikingly different from the mixed monolayers containing EG4N: No change in twist angle was observed over the entire range of solution compositions for the mixed monolayers of AET and EG4 (FIG. 12). This result indicates the absence of measurable incorporation of AET into the SAM formed on the gold film. This result is consistent with our prediction that AET, in contrast to EG4N, does not compete effectively with EG4 during formation of the mixed SAMs due to its small size relative to EG4 (cohesive interactions within SAMs increase with size of the molecules forming the SAMs).

Example 5

Anchoring Energy Measurements

Figure 14:
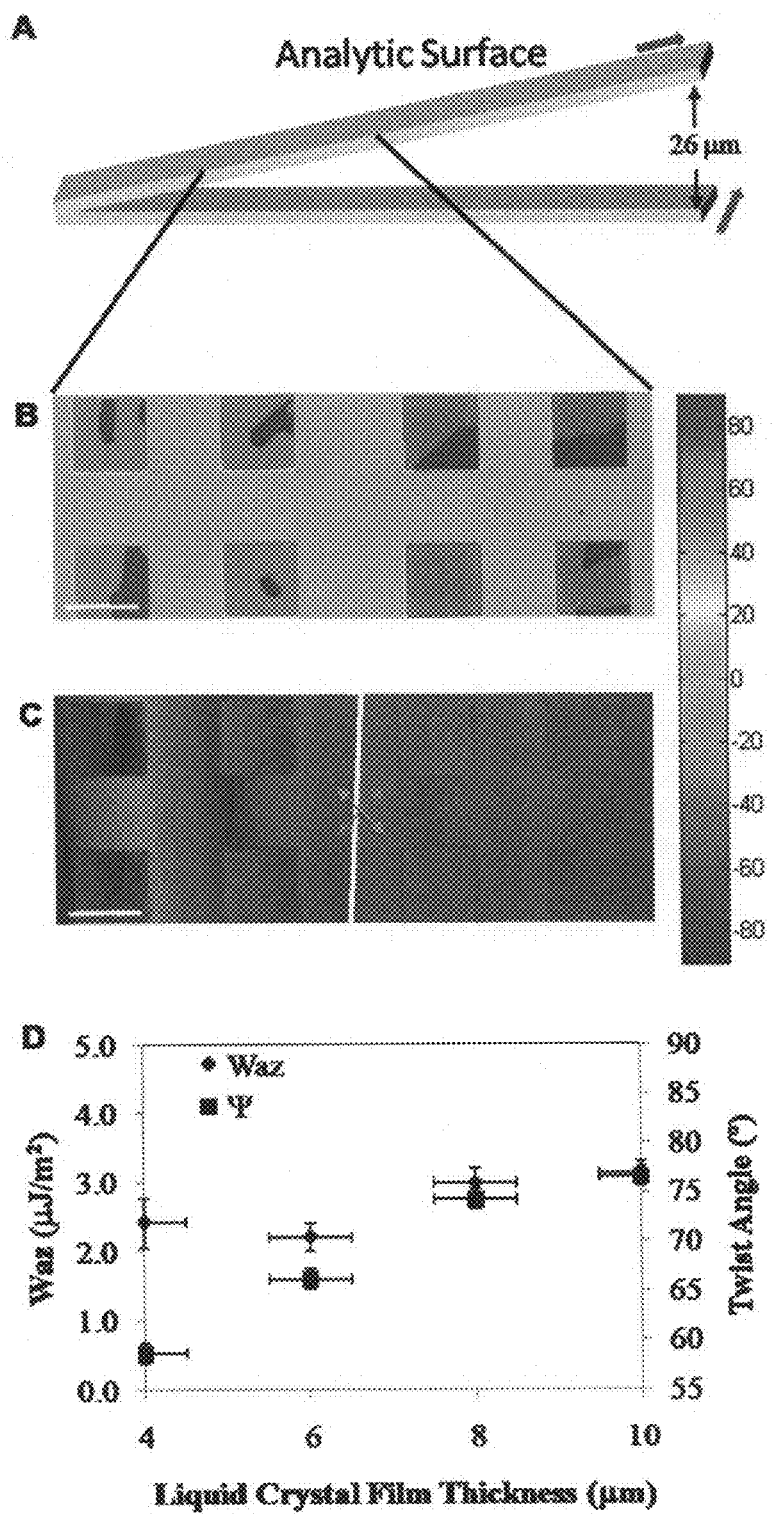
FIG. 14. (A) Schematic illustration of a TNLC cell with a gradient in thickness of the LC across the cell. The direction of deposition of the gold film on the analytic (top) and reference surface (bottom) is indicated by the gray arrows. The analytic surface was microcontact printed with hexadecanethiol, and the unreacted regions (squares) were functionalized with EG4. (B) Map of twist angles across the analytic surface. Twist angles of the LC corresponding to each color are indicated by the color chart shown at the right side of the figure. (C) Interference images of the LC used to calculate the thickness of the LC cell. (D) Twist angles and anchoring energies plotted as a function of the LC film thickness. Scale bars represent 1 mm.

As demonstrated above, maps of the LC twist angle can provide information about the spatial variation of chemistry across an analytic surface. The twist angle adopted by TNLCs, however, is influenced by the geometry of the optical cell (namely, the film thickness, d) as well as the properties of the surfaces confining the LC. In contrast, the azimuthal anchoring energy calculated according to Eq. (1) is a physical property that characterizes the surface interaction with the LC, independent of the sample geometry. To illustrate the potential value of creating spatial maps of anchoring energy (as opposed to maps of twist angles), the inventors fabricated an optical cell with the EG4 chemistry patterned across the analytic surface (as described above) but with a variable LC film thickness across the optical cell (FIG. 14A). The squares on the analytical surface were functionalized by immersion into an ethanolic solution of EG4 for 2 hours and the analytic surface and reference surface were oriented at 90° to each other.

As described previously, the inventors used interference colors (FIG. 14C) that result when the optical cell is viewed between crossed polarizers to determine the thickness of the LC. Clare, B. H. et al.; *Langmuir* 2006, 22, 4654-4659; Clare, B. H. et al.; *Langmuir* 2006, 22, 7776-7782. FIG. 14D shows both twist angles and anchoring energies calculated from the twist angles and LC thicknesses. Within the area of the LC cell that was analyzed, the thickness of the LC film ranged from ~4 μm to 10 μm. Inspection of FIG. 14D shows that within this region the twist angle increased with LC film thickness whereas the anchoring energy was calculated to be constant. This result demonstrates that the methodology reported herein can also be used to calculate maps of anchoring energies of LCs on patterned surfaces. The inventors note that the values of the anchoring energy shown in FIG. 14D (2.2-3.1 $\mu J/m^2$) are lower than those reported previously for SAMs for EG4 (5.3 $\mu J/m^2$). This result is not unexpected because the SAMs were formed for different times (2 hrs versus 18 hrs) in the two sets of experiments. SAMs prepared using short immersion times are expected to be less ordered, particularly EG-terminated SAMs, and thus will lead to lower anchoring energies.

Example 6

Imaging of Surfaces Presenting Affinity Microcontact Printed Antibodies

Previously, it was reported that LCs can be used to image proteins captured and delivered to surfaces by using affinity microcontact printing. Bernard, A. et al.; *Nat. Biotechnol.* 2001, 19, 866-869. Whereas past interpretation of the LC optical appearance was qualitative in nature, here the inventors demonstrate that twisted LC cells can be used in combination with affinity microcontact printing to achieve quantitative measurements of printed patterns of proteins. The inventors covalently linked biotinylated BSA onto patterned PDMS stamps and used the stamps to capture anti-biotin IgG (with anti-rabbit IgG serving as a negative control). Captured IgG molecules were then microcontact printed onto monolayers formed from AET on gold films deposited at an angle of 30° relative to the surface normal. Inspection of FIG. 15A reveals that the analytic surface onto which anti-biotin IgG was printed caused the LC to adopt a complicated pattern of twist angles that radiated from a central point. In contrast, the analytic surface onto which the anti-rabbit control antibody was printed (FIG. 15B) displayed uniform twist angles that were indistinguishable from background, indicating no measurable anti-rabbit IgG was transferred to the analytic surface.

Figure 15:
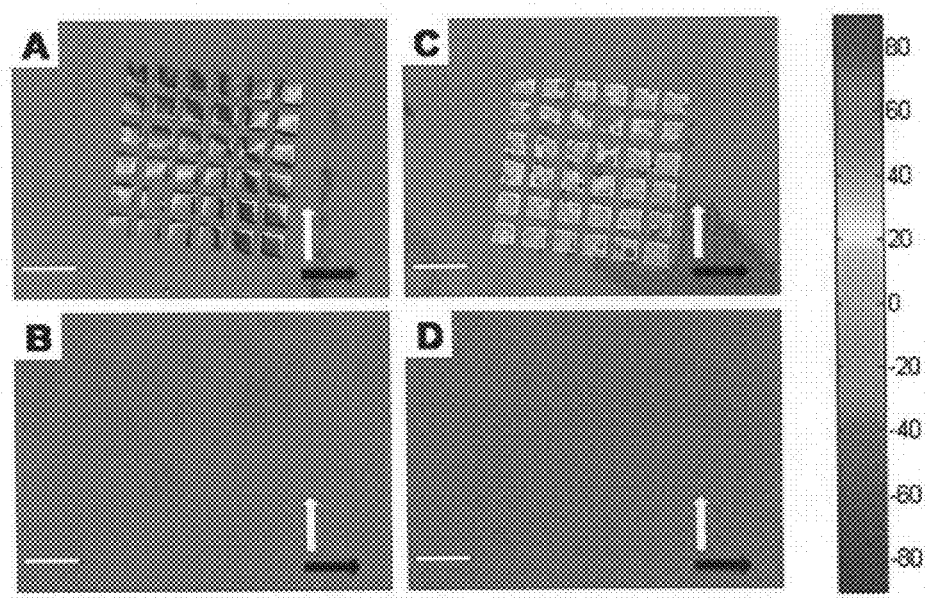
FIG. 15. Maps of twist angles obtained using analytic surfaces on which anti-biotin IgG was affinity microcontact printed (A and C). The maps of twist angles shown in B and D are the results of control experiments performed using anti-rabbit IgG. For C and D, the antibody was rinsed with water prior to forming the TNLC cell. The direction of deposition of the gold film used for the analytic and reference surface is indicated by the white and black arrows, respectively. Twist angles of the LC corresponding to each color are indicated by the color chart shown at the right side of the figure. Scale bars represent 1 mm.

The inventors speculated that the radial pattern evident in FIG. 15A was caused by shear forces acting on the IgG molecules during the drying of the stamp under the gaseous stream of nitrogen (the stream was directed to the center of the stamp). Although prior studies demonstrate that the process of contact of the PDMS stamp with the surface can induce organization into the stamped proteins that orients LCs (Tingey, M. L. et al., *Adv. Mater.* 2004, 16, 1331-1336), they do not believe that the manner of contact of the stamp with the surface led to the pattern in FIG. 10A because the stamp was brought into contact with the surface at normal incidence. The inventors speculated that a brief rinse of the analytic surface with water after contact printing might erase the radial pattern evident in FIG. 15A. To test this proposition, they stamped anti-biotin IgG or anti-rabbit IgG onto an AET-functionalized surface, briefly rinsed the surface with deionized water adjusted to pH 5.0 with HCl, and then dried the surface under a stream of nitrogen gas. FIGS. 15C and 15D (control) show that this modified procedure does lead to elimination of the radial pattern.

The above results illustrate the utility of methods based on TNLCs for imaging proteins printed on surfaces. In particular, the TNLC-based method enabled identification of the likely source of an initially complex response of the LC to the printed proteins. The inventors note that analysis of individual optical images of the LC did not lead to an obvious suggestion regarding the possible origins of the complex patterns on the surface. The patterns of twist angle suggested the origin of the non-uniformity to be the gaseous stream used to dry the proteins on the stamp. A simple rinse of the printed proteins was found to be sufficient to erase the complex pattern, thus permitting the use of the TNLCs to provide clear maps of the location of the antibodies printed on the surface.

Example 7

Analysis of Surfaces Used to Prepare Protein Microarrays

The current invention can be used to perform quality control on surfaces used to create protein microarrays and other surface-based analytic devices and methods. In this example, two analytic surfaces are produced by obliquely depositing gold at an angle of 49° onto glass surfaces. The gold surfaces are functionalized via immersion into 1 mM (total concentration) ethanolic solutions of thiols (99% $HSC_{11}EG_4OH$, 1% $HSC_{11}EG_4NH_2$) for 18 hr. Two reference surfaces are produced by obliquely depositing gold at an angle of 64° onto glass surfaces. These gold surfaces are then functionalized by immersion into 1 mM solutions of $HSC_{15}$ for 18 hr. As described above, the reference and analytic surfaces are used to construct two liquid crystal cells, which are analyzed using the automated analysis algorithm. The analysis reveals that one analytic surface is spatially homogeneous in its alignment of the liquid crystal, while the other analytic surface has many areas that present varying degrees of twist in the liquid crystal. The surface with heterogeneities is discarded as being of poor quality for microarray purposes, while the homogenous surface continues to be processed for microarray usage. The homogenous surface is recovered for further functionalization by rinsing the liquid crystal from the surface with acetone. Using a bis(sulfosuccinimidyl)suberate ($BS^3$) linker, biotinylated BSA is immobilized onto the surface. The surface with biotinylated BSA on the surface is incubated with an aqueous solution of antibiotin IgG (goat, 1 micromolar in PBS) and the resulting surface is quantified with the automated twist analysis technique. By using the automated analysis technique before protein immobilization and after antibody capture, accurate and reproducible results are found. In the absence of the quality control step in the preparation of the surfaces, the results obtained with the antibody binding are not highly reproducible. This example illustrates how the methodology can be used to perform quality control on surfaces used in analytical devices.

Example 8

Optimizing Sensitivity by Varying Liquid Crystal Thickness and Other Parameters

Figure 16:
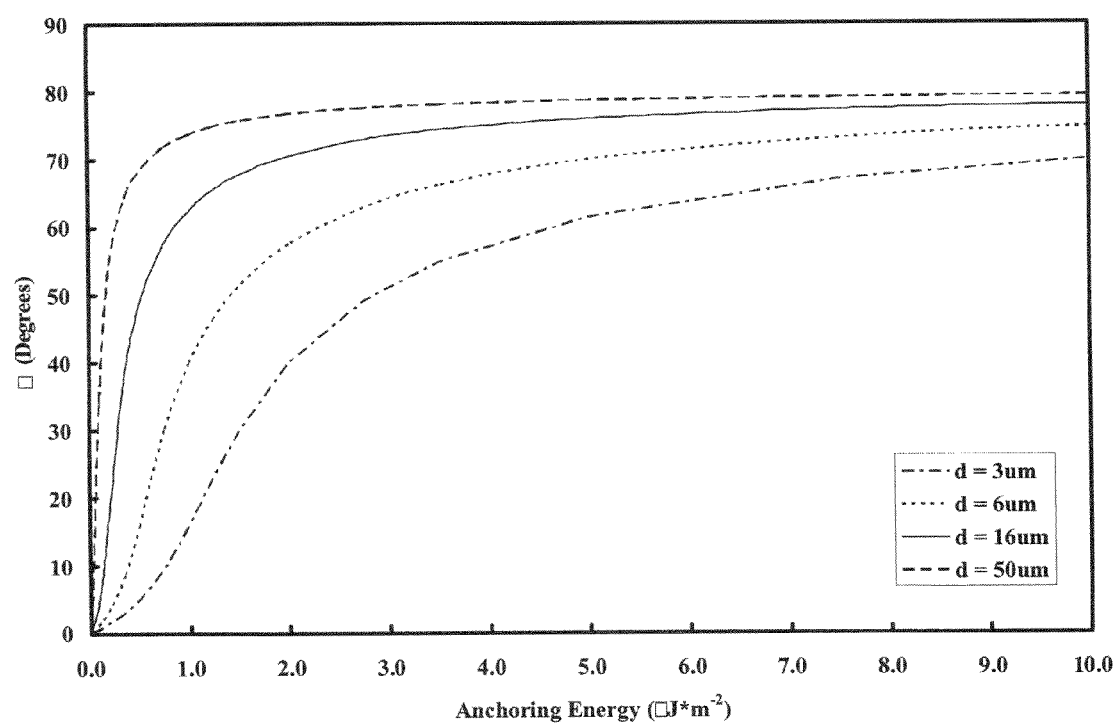
FIG. 16: Liquid crystal twist angle versus anchoring energy for different thicknesses of liquid crystals obtained by solving equation (1).

Factors Affecting Twist Angles. Liquid crystal twist angles are determined by multiple factors (See Eq. (1) above). In this example, the inventors have identified preferred values of these factors. Three key factors that will influence the amount of twist of the liquid crystal are the azimuthal anchoring energy of each aligning surface, the thickness of the liquid crystal cell and the orientation of the easy axis of each aligning surface. For example, FIG. 16 shows a plot of twist versus anchoring energy for a range of anchoring energy values and LC thicknesses. As the anchoring energy increases, the error propagated as a result of small errors in the measurement of the twist value becomes more substantial until it is not possible to accurately make a determination of the anchoring energy based upon twist angle measurements. Because of the increased error for twist values with greater anchoring energy, the upper limit of the preferred anchoring energy range is ~10 $\mu J/m^2$. The lower limit of the preferred range for anchoring energy used in twist measurements is similarly defined, as extremely small anchoring energies give rise to such small twist values that they cannot be accurately determined within the error of measurement provided by the technique used in the invention. Accordingly, the smallest preferred anchoring energy value for use in the invention is ~0.01 $\mu J/m^2$.

These lower and upper bounds to the preferred values define the range of anchoring energies that are preferred, but further considerations define additional preferred parameter values for protein detection. If an analytical surface is fabricated such that it possesses an anchoring energy of 10 $\mu J/m^2$, then a very small change in anchoring energy caused by minute amounts of protein adsorbed onto the surface will not be easily measured. For example, if a reduction in anchoring energy of 0.5 $\mu J/m^2$ occurs upon adsorption of a sub-monolayer of protein on an analytical surface possessing an anchoring energy of 10 $\mu J/m^2$, the corresponding change in twist would be only 0.04°. Because such a small change in twist angle would require very precise determination of twist angles, a more appropriate anchoring energy must be chosen as the initial starting point. Preferably a change of several degrees will occur upon adsorption of a protein molecule to the analytical surface. Therefore, a more preferred upper limit of the surface anchoring energies used in the invention is 5 $\mu J/m^2$.

There exists a range of anchoring energy values where the twist angle changes very rapidly with only modest changes in the anchoring energy. This range is dependent upon the thickness of the liquid crystal cell, and for a thickness of 16 μm, it spans from 0.01-2 $\mu J/m^2$. For the purposes of protein detection, knowledge of such a sensitive regime is beneficial, and the inventors sought to define a set of experimental conditions that would allow access to this regime.

Figure 17:
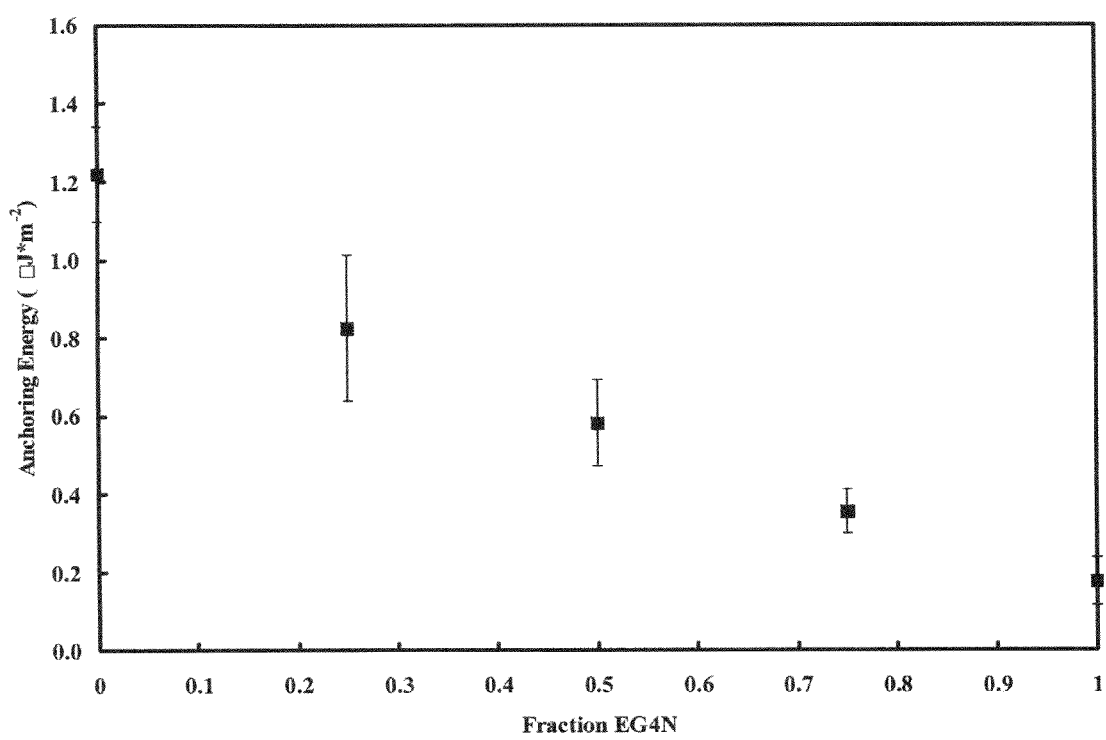
FIG. 17: Azimuthal anchoring energy versus fraction EG4N for mixed EG4/EG4N SAMs formed on gold films deposited at 30° relative to the surface normal. Error bars represent standard deviations for n>3.

Varying Parameters to Optimize Sensitivity. In order to define a surface that would allow access to the most sensitive and accurate range of anchoring energies, the inventors measured anchoring energies for surfaces fabricated with a constant angle of gold deposition, but with different SAM compositions. FIG. 17 shows anchoring energy measurements for gold deposited at 30° to the surface normal, and with SAMs that were formed from solutions containing mixtures of EG4 and EG4N. The anchoring energy was observed to decrease in a linear fashion from 1.2 $\mu J/m^2$ to 0.17 $\mu J/m^2$ as the mole fraction of EG4N increased from 0 to 1.

Figure 18:
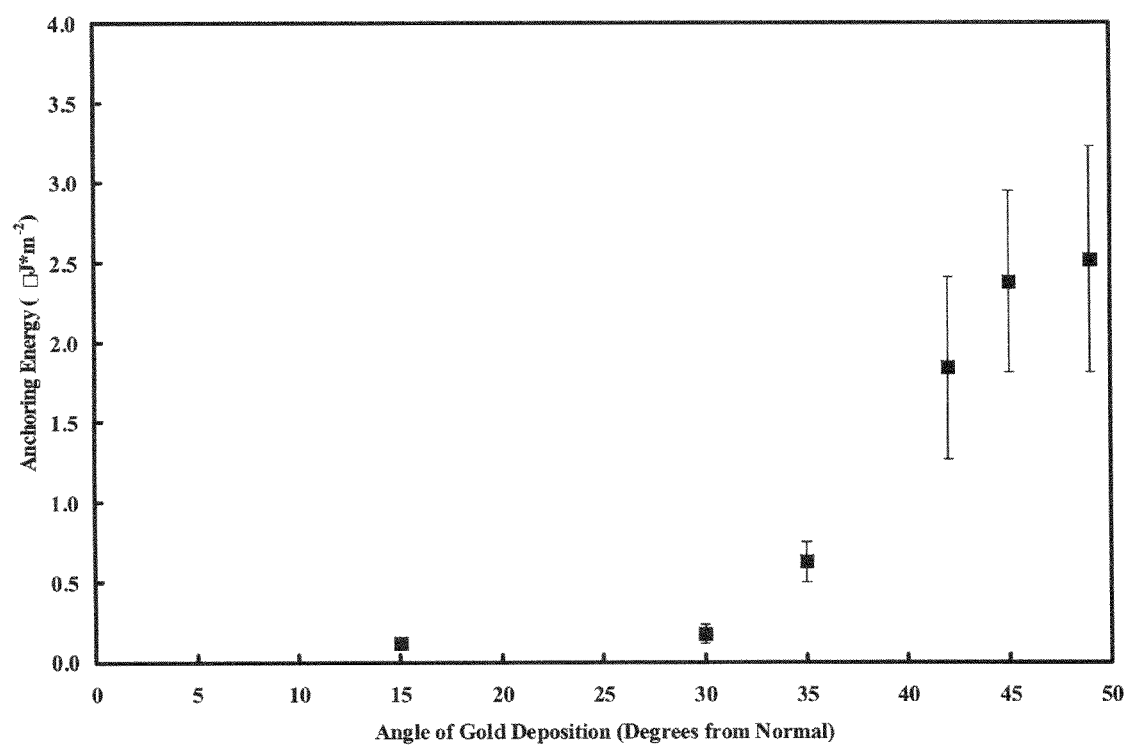
FIG. 18: Azimuthal anchoring energy versus angle of gold deposition for surfaces functionalized with EG4N SAMs. Error bars represent standard deviations for n>3.

The inventors also characterized surfaces with constant SAM compositions while varying the angle of gold deposition. FIG. 18 shows that for surfaces functionalized with EG4N, anchoring energy is a strong function of the angle of gold deposition from 30° to 49°. Over this range of deposition angles, the anchoring energy increased from 0.17 $\mu J/m^2$ to 2.5 $\mu J/m^2$ in a nearly linear fashion.

The inventors hypothesized that surfaces fabricated such that the anchoring energy is <1 $\mu J/m^2$ would provide greater sensitivity when used as part of a liquid crystal detection device when the thickness of the liquid crystal is 16 μm. To test this hypothesis, the inventors affinity captured EGFR as described previously (Lowe, A. M et al., *Lab Chip*, 8, 1357-1364, 2008) and transferred it by direct physical contact to the surface of (i) gold deposited at an angle of incidence of 35° and functionalized with EG4N and (ii) gold deposited at an angle of incidence of 49° and functionalized with EG4N. Based on our observations summarized in FIG. 18, we predicted that gold deposited at 35° and functionalized with EG4N would have an anchoring energy of 0.6 $\mu J/m^2$ and gold deposited at 49° would have an anchoring energy of 2.5 $\mu J/m^2$. According to our hypothesis, the 35° surface should then allow for greater relaxation of liquid crystal twist when the surface is covered with protein molecules.

Figure 19:
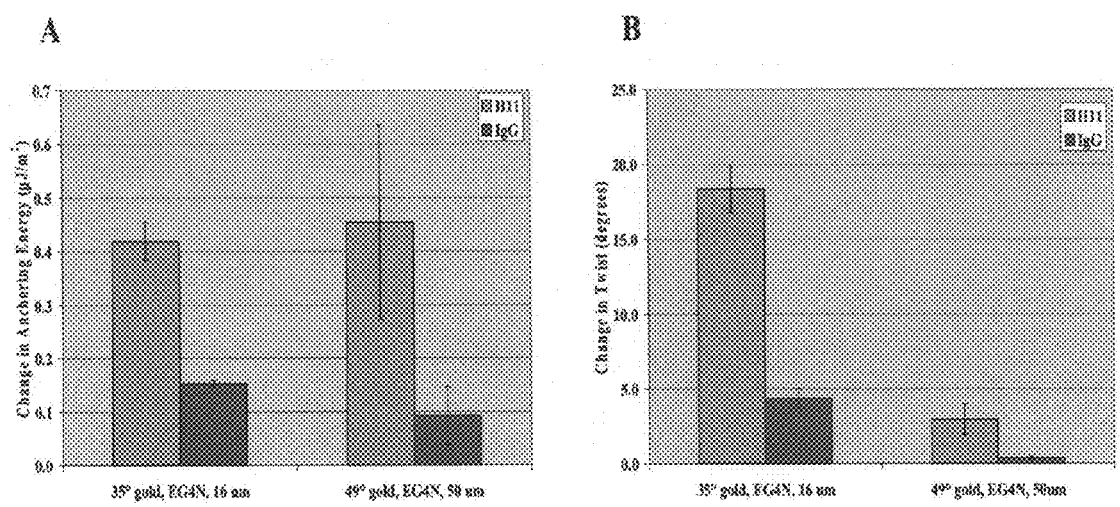
FIG. 19: Liquid crystal response to affinity contact printed EGFR. H11 is an anti-EGFR IgG that captured the receptor from solution and IgG is an isotype control antibody. (A) The reduction in azimuthal anchoring energy in regions where EGFR was transferred. (B) The reduction in liquid crystal twist in regions where the EGFR was transferred. Error bars represent standard error of the mean (n>4).

After affinity contact printing, the 35° surface was fabricated into a twisted liquid crystal cell by pairing the 35° surface with a 64° slide functionalized with pentadecanethiol, using 16 μm mylar spacers as previously described. The 49° surface was similarly fabricated into a twisted liquid crystal cell using 50 μm spacers. Each liquid crystal device was then analyzed using the automated analysis technique already described, with several replicates performed for each sample condition. EGFR capture and transfer to the surfaces was confirmed with $^{32}P$ radiolabeling, as described previously. Lowe, A. M. et al., *Lab Chip*, 8, 1357-1364, 2008, which is incorporated by reference herein. The anchoring energy reduction caused by the presence of the EGFR for each surface is reported in FIG. 19(*a*), and the corresponding change in twist angle is reported in FIG. 19(*b*). We observed that the average anchoring energy was reduced by ~0.4 $\mu J/m^2$ for areas stamped with EGFR on each surface. The corresponding reduction in the twist angle was observed to be ~18° for the 35° surface with 16 μm spacers, while the decrease was a modest 3° for the 49° surface with 50 μm spacers. These results, when taken together support the proposition that liquid crystal devices can be designed and fabricated for maximum sensitivity and precision by varying parameters such as gold topography (deposition angle), liquid crystal thickness and SAM composition.

Example 9

Optimizing Sensitivity Through Temperature Control

As explained in the previous section, for small amounts of protein on the analytical surface (sub-monolayer), the azimuthal anchoring energy of the analytical surface changes by a small increment (~0.5 μJ/m$^2$). If the amount of protein approaches monolayer coverage, the azimuthal anchoring energy can be lowered to such an extent that no twist in the liquid crystal is observed. In order to maintain some level of measurable twist, it would be desirable to fabricate a surface possessing an anchoring energy that is high enough to prevent the twisted liquid crystal in contact with the protein-laden analytical surface from relaxing measurably (2.5 μJ/m$^2$, for example). The anchoring energy would then be systematically reduced after the fabrication of a liquid crystal device, until an anchoring energy appropriate for protein detection is reached. By inserting the liquid crystal cell into a temperature control device with an aperture for light transmission, this can be accomplished. Faetti, S. et. al.; *Phys. Rev. Lett.* 1985, 55(16), 1681-1684, which is incorporated by reference herein.

A proposed experiment using this technique would proceed as follows. A reference surface is fabricated as previously described by evaporating gold onto a glass slide at an angle of 64° relative to the surface normal. The slide is then incubated in a solution of 1 mM pentadecanethiol in ethanol for 18 hours. An analytical surface is fabricated by evaporating gold onto a glass slide at an angle of 49° relative to the surface normal. The analytical surface is then incubated in a solution of 1 mM EG4N in ethanol for 18 hours. The reference surface and analytical surfaces are both removed from the thiol solution and rinsed sequentially in ethanol, water and ethanol. The analytical surface is then immersed into a 0.01 M HCl solution for 30 s and dried under a stream of nitrogen. H11 anti-EGFR antibody (Labvision) is immobilized onto an affinity stamp, prepared as described previously. Lowe, A. M. et al., *Lab Chip*, 8, 1357-1364, 2008, which is incorporated by reference herein. The affinity stamp is then incubated with a 5 nM solution of epidermal growth factor receptor (EGFR) in phosphate buffered saline (PBS) for two hours. The affinity stamp is then rinsed sequentially with PBS containing 0.05% tween-20 and PBS followed by drying under a stream of nitrogen. The affinity stamp is then placed into conformal contact with the analytical surface for 5 min, slowly peeled away and the analytical surface is briefly immersed into 0.01 M HCl.

A liquid crystal cell is then constructed as previously described, using 16 μm mylar spacers to separate the analytical surface and reference surface. The liquid crystal cell is then inserted into a temperature control chamber possessing an aperture for the transmission of light. The chamber is inserted between the analyzer and polarizer of a polarized light microscope. Twist measurements are then taken using the previously described procedure at temperatures ranging from 25-35° C. (35° C. is the nematic to isotropic transition temperature of 5CB).

The anchoring energy of the liquid crystal to the analytical surface is dependent upon the temperature of the liquid crystal, and becomes lower as the temperature approaches the nematic to isotropic phase transition temperature. At 25° C., the anchoring energy of the neat EG4N SAM on 49° gold is ~2.5 μJ/m$^2$. However, as the temperature approaches 35° C., the anchoring energy lowers until it is no longer meaningful to make a measurement. At a temperature of 25° C., the quantity of EGFR deposited onto the analytical surface lowers the anchoring energy of the neat EG4N surface from ~2.5 μJ/m^2 to ~2.0 μJ/m^2, and the corresponding change in measured twist angle is only ~4°. However, as the temperature is raised, the anchoring energy of the neat EG4N surface becomes ~0.8 μJ/m^2, and is lowered to ~0.3 μJ/m^2 in regions where EGFR have been deposited, which corresponds to change in twist angle of 18°. Thus, the anchoring energy is lowered by the same amount for a given quantity of EGFR at any temperature, but the observed variable (namely, the twist) is lowered by different amounts at different temperatures. The anchoring energy of the analytical surface is thus tuned to yield a response that is more accurately measured, allowing for greater resolution with respect to quantification of anchoring energy and by extension, the quantity of protein present.

Overall, the foregoing results establish general and versatile methods for data acquisition and image analysis that permit the use of TNLCs to create maps of bio/chemical functionality patterned on surfaces. The method involves the acquisition of a series of images (transmission mode between two polarizers) of a film of a TNLC that contacts the analytic surface and analysis of the stack of images to yield maps of twist angle of the LC across the surface. This analysis technique effectively condenses a large data set (stack of images) into a compact form (map of twist angle), revealing features on the surface that were not apparent in the individual images comprising the original stack. The utility of the approach for characterization of patterned surface chemistry was demonstrated by following (i) the displacement of a SAM formed from an alkanethiol on a gold film by a second alkanethiol in solution, (ii) coadsorption of mixtures of organothiols with chemical functionality relevant to bioanalytical surfaces, and (iii) the presence of antibodies printed onto surfaces. The twist angles of the LC can be used to quantify the energy of interaction of the LC with the surface with a spatial resolution of <10 μm. Accordingly, maps of twist angle created by TNLCs provide the basis of methods that can be used to monitor and validate chemical modifications of surfaces that are employed in surface-based analytical technologies.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. All publications, patents and patent applications cited herein are hereby incorporated by reference in their entirety for all purposes.

What is claimed is:

1. An analysis system for determining the distortion of a liquid crystal as a function of position across a surface, comprising:
   (a) a liquid crystal cell including a liquid crystal positioned between an analyte surface and a reference surface, said surfaces spaced apart from each other such that the analyte surface orients the liquid crystal with an orientation that differs from the reference surface thereby introducing a distortion in the liquid crystal; and (b) an automated imaging system including:
  (i) an adjustable polarized light source to provide polarized light incident to the liquid crystal cell;
  (ii) an analyte linear polarizing device positioned to receive light passed through the liquid crystal cell, said analyte linear polarizing device adjustable with respect to polarization direction;
  (iii) an imaging device positioned to receive light passed through the analyte linear polarizing device from the liquid crystal cell; and
  (iv) one or more computer(s) interfaced with the analyte linear polarizing device, the computer(s) capable of receiving multiple image data from the imaging device and analyzing the multiple image data to determine the distortion of the liquid crystal contained within the liquid crystal cell as a function of position across one of the surfaces.

2. The analysis system according to claim 1, wherein the computer is capable of automatically adjusting the polarization direction of the analyte linear polarizing device through the interface with the analyte linear polarizing device.

3. The analysis system according to claim 1, wherein the distortion present in the liquid crystal contained in said liquid crystal cell is restricted to the in-plane orientation.

4. The analysis system according to claim 1, wherein the distortion present in the liquid crystal contained in said liquid crystal cell is a twist distortion of the liquid crystal.

5. The analysis system according to claim 1, wherein said imaging device comprises a digital camera, a charge coupled array, an optical scanner, or a photomultiplier tube array.

6. The analysis system according to claim 1, further comprising a positioning stage capable of controlling x-y movement of the liquid crystal cell.

7. The analysis system according to claim 1, wherein the liquid crystal positioned between the analyte surface and the reference surface has a thickness from about 3 μm to about 50 μm.

8. The analysis system according to claim 7, wherein the thickness of the liquid crystal positioned between the two surfaces is at least about 6 μm.

9. The analysis system according to claim 8, wherein the thickness of the liquid crystal positioned between the two surfaces is about 15 μm.

10. The analysis system according to claim 1, wherein the analyte surface comprises an analyte that has been attached to the analyte surface through affinity microcontact printing.

11. The analysis system according to claim 1, further comprising a temperature control device capable of controlling the temperature within the liquid crystal cell.

12. The analysis system according to claim 1, wherein the reference surface in the liquid crystal cell is an interface between the liquid crystal and air.

13. The analysis system according to claim 1, wherein the distortion of the liquid crystal contained within the liquid crystal cell as a function of position across one of the surfaces is provided by one or more computers as a spatial map of the distortion of the liquid crystal.

14. The analysis system according to claim 1, wherein the liquid crystal cells are analyzed to determine if the analytic surface causes a desired alignment of the liquid crystal.

15. A method for determining the distortion of a liquid crystal as a function of position across a surface, comprising the steps of:

(a) acquiring multiple polarized light images of a liquid crystal contained within a liquid crystal cell; and
(b) condensing the multiple polarized light images to provide a data set describing the distortion of the liquid crystal contained within the liquid crystal cell as a function of position across a surface of the liquid crystal cell.

16. The method according to claim 15, wherein the liquid crystal is held stationary as the polarization direction of polarized light is changed to collect the multiple polarized light images of the liquid crystal.

17. The method according to claim 16, wherein the temperature of the liquid crystal is controlled to optimize the sensitivity of the method.

18. The method according to claim 15, wherein the method further comprises the step of providing an analysis system according to claim 1 to carry out steps (a) and (b).

19. The method according to claim 15, wherein the data set describing the distortion of the liquid crystal contained within the liquid crystal cell as a function of position across a surface of the liquid crystal cell is in the form of a spatial map.

20. A method for determining the anchoring energy of a liquid crystal in contact with a surface as a function of position across the surface, comprising:

(a) acquiring multiple polarized light images of a liquid crystal contained within a liquid crystal cell;
(b) condensing the multiple polarized light images to provide spatially resolved data for the distortion of the liquid crystal contained within the liquid crystal cell;
(c) providing spatially resolved data for the thickness of the liquid crystal positioned between two surfaces of the liquid crystal cell; and
(d) using the spatially resolved distortion data and the spatially resolved thickness data to determine the anchoring energy of the liquid crystal in contact with one of the surfaces of the liquid crystal cell as a function of position across the surface.

21. The method according to claim 20, wherein the anchoring energy of the liquid crystal in contact with one of the surfaces of the liquid crystal cell as a function of position across the surface is provided in the form of a spatial map.

22. The method according to claim 20, wherein UV-visible absorption measurements are used to provide the spatially resolved data for the thickness of the liquid crystal positioned between the two surfaces of the liquid crystal cell.

23. The method according to claim 20, wherein the method further comprises the step of providing an analysis system according to claim 1 to carry out steps (a)-(d).

24. An analysis system for determining the distortion of a liquid crystal as a function of position across a surface, comprising:

(a) a liquid crystal cell including a liquid crystal positioned between an analyte surface and a reference surface, said surfaces spaced apart from each other such that the analyte surface orients the liquid crystal with an orientation that differs from the reference surface thereby introducing a distortion in the liquid crystal; and
(b) a means for acquiring multiple polarized light images of the liquid crystal contained within the liquid crystal cell and for condensing the multiple polarized light images to provide a data set describing the distortion of the liquid crystal contained within the liquid crystal cell as a function of position across one of the surfaces.

* * * * *

UNITED STATES PATENT AND TRADEMARK OFFICE
CERTIFICATE OF CORRECTION

PATENT NO.        : 8,125,640 B2
APPLICATION NO.   : 12/380751
DATED             : February 28, 2012
INVENTOR(S)       : Abbott et al.

It is certified that error appears in the above-identified patent and that said Letters Patent is hereby corrected as shown below:

Column 10, line 6 "ϕ" should be --φ--

Column 18, line 29 "250 mL" should be --250 nL--

Column 18, line 47 "ϕ" should be --φ--

Column 18, line 65 "ϕ" should be --φ--

Signed and Sealed this
Twenty-ninth Day of May, 2012

David J. Kappos
*Director of the United States Patent and Trademark Office*